US010003944B2

(12) United States Patent
Choi et al.

(10) Patent No.: US 10,003,944 B2
(45) Date of Patent: Jun. 19, 2018

(54) ELECTRONIC DEVICE AND METHOD FOR PROVIDING EMERGENCY VIDEO CALL SERVICE

(71) Applicant: Samsung Electronics Co., Ltd., Gyeonggi-do (KR)

(72) Inventors: Woo-Jun Choi, Gyeonggi-do (KR); Ju-Seung Lee, Gyeonggi-do (KR); Soon-Hyun Cha, Gyeonggi-do (KR); Sun-Min Hwang, Gyeonggi-do (KR)

(73) Assignee: Samsung Electronics Co., Ltd., Yeongton-gu, Suwon-si, Gyeonggi-do (KR)

( * ) Notice: Subject to any disclaimer, the term of this patent is extended or adjusted under 35 U.S.C. 154(b) by 0 days. days.

(21) Appl. No.: 14/699,159

(22) Filed: Apr. 29, 2015

(65) Prior Publication Data
US 2015/0312742 A1 Oct. 29, 2015

(30) Foreign Application Priority Data

Apr. 29, 2014 (KR) .................. 10-2014-0051780

(51) Int. Cl.
*A61B 5/00* (2006.01)
*H04W 4/02* (2018.01)
(Continued)

(52) U.S. Cl.
CPC ............. *H04W 4/22* (2013.01); *A61B 5/0022* (2013.01); *A61B 5/0205* (2013.01);
(Continued)

(58) Field of Classification Search
CPC ....... H04W 4/22; H04W 4/12; H04W 76/007; H04W 8/22; H04W 84/12; H04W 4/008;
(Continued)

(56) References Cited

U.S. PATENT DOCUMENTS 6,778,661 B1 * 8/2004 Yumoto ............ H04L 29/06027
370/270
7,076,211 B2 * 7/2006 Donner .................... H04Q 9/00
340/506

(Continued)

FOREIGN PATENT DOCUMENTS

EP 1835778 A1 * 9/2007 ........ H04M 3/42382
EP 2 711 906 A2 3/2014
(Continued)

OTHER PUBLICATIONS

European Search Report dated Nov. 7, 2017.
European Search Report dated Feb. 8, 2018.

*Primary Examiner* — Olumide T Ajibade Akonai
(74) *Attorney, Agent, or Firm* — Cha & Reiter, LLC

(57) ABSTRACT

Disclosed herein are an electronic device and a method executable therein. The electronic device includes a communication module, and a processor executing the method, which includes detecting the generation of a specific event, controlling the communication module to transmit a message to one or more other electronic devices located within a predetermined range, and control the communication module to communicate with the one or more other electronic devices based on a request from the one or more second electronic devices.

15 Claims, 13 Drawing Sheets

(51) Int. Cl.
  *H04W 4/90* (2018.01)
  *H04W 4/22* (2009.01)
  *H04W 4/00* (2018.01)
  *A61B 5/0205* (2006.01)
  *A61B 5/11* (2006.01)
  *A61B 5/1171* (2016.01)
  *H04L 29/08* (2006.01)

(52) U.S. Cl.
  CPC ........... *A61B 5/1112* (2013.01); *A61B 5/1176* (2013.01); *A61B 5/6898* (2013.01); *A61B 5/747* (2013.01); *H04L 67/12* (2013.01); *H04W 4/005* (2013.01); *H04W 4/008* (2013.01); *H04W 4/02* (2013.01); *H04W 4/70* (2018.02); *H04W 4/80* (2018.02); *H04W 4/90* (2018.02)

(58) Field of Classification Search
  CPC ......... H04W 4/04; H04W 4/14; H04W 76/02; H04W 76/025; H04W 4/16; H04W 4/02; H04W 4/18; H04W 84/18; H04W 4/023; H04W 4/021; H04W 4/206; H04W 4/08; H04W 64/00; H04W 4/027; H04W 4/025; H04M 1/7253; H04M 2250/02; H04M 3/5116; H04M 2242/30; H04M 2242/04; H04L 51/38; H04L 51/04; H04L 51/32; H04L 51/10; H04L 67/14; H04L 12/1818; H04L 12/588; H04L 51/36; H04L 65/1069; H04L 65/403; H04L 67/18; H04L 67/22; H04L 51/20; H04N 7/15; H04N 7/141; H04N 2007/145; H04N 21/41407; H04N 7/147; H04N 21/2187; H04N 21/8586; H04N 21/814; G06Q 50/01; G06Q 30/0261; G06Q 20/3224; G06Q 30/0267; G06Q 50/24; G06F 19/3418; G06F 19/3487; G06F 19/345; G06F 19/3425; G01S 5/0252; A61B 5/0006; A61B 5/0205; A61B 5/08; A61B 5/021; A61B 5/0015; A61B 5/0022; A61B 5/02405
  USPC .............. 455/404.1, 404.2, 466, 41.2, 518; 370/338
  See application file for complete search history.

(56) References Cited

U.S. PATENT DOCUMENTS

| | | | |
|---|---|---|---|
| 7,844,247 B2* | 11/2010 | Chen | G08G 1/205 455/404.1 |
| 8,200,185 B2 | 6/2012 | Edge et al. | |
| 8,238,870 B2* | 8/2012 | Xing | H04L 12/189 379/37 |
| 8,428,548 B2 | 4/2013 | Ray et al. | |
| 2007/0213600 A1* | 9/2007 | John | A61B 5/0031 600/300 |
| 2008/0212746 A1* | 9/2008 | Gupta | G06F 19/3418 379/38 |
| 2008/0214903 A1* | 9/2008 | Orbach | A61B 5/486 600/301 |
| 2008/0254811 A1* | 10/2008 | Stewart | H04M 1/72572 455/456.2 |
| 2008/0266118 A1* | 10/2008 | Pierson | A61B 5/0205 340/573.6 |
| 2009/0286504 A1 | 11/2009 | Krasner et al. | |
| 2010/0062741 A1* | 3/2010 | Lee | H04M 1/72552 455/404.1 |
| 2010/0099461 A1* | 4/2010 | Rahfaldt | H04M 1/72541 455/557 |
| 2010/0194525 A1* | 8/2010 | Do | G08B 21/0461 340/5.1 |
| 2011/0063105 A1 | 3/2011 | Bennett et al. | |
| 2011/0111728 A1* | 5/2011 | Ferguson | H04M 1/72541 455/404.2 |
| 2011/0270096 A1* | 11/2011 | Osorio | A61B 5/02405 600/483 |
| 2011/0300879 A1* | 12/2011 | Braun | G08B 25/016 455/456.1 |
| 2012/0134345 A1* | 5/2012 | Tamhankar | H04W 4/22 370/338 |
| 2013/0122853 A1 | 5/2013 | Penix et al. | |
| 2013/0331058 A1 | 12/2013 | Harvey | |
| 2014/0045547 A1 | 2/2014 | Singamsetty et al. | |
| 2014/0055553 A1* | 2/2014 | Lee | G06K 9/00288 348/14.07 |
| 2014/0080415 A1 | 3/2014 | Black et al. | |
| 2015/0029295 A1* | 1/2015 | Gupta | H04M 3/5116 348/14.01 |
| 2015/0172894 A1* | 6/2015 | Gabel | H04W 4/22 455/404.2 |

FOREIGN PATENT DOCUMENTS

| | | |
|---|---|---|
| JP | 2013-59067 A | 3/2013 |
| KR | 10-2005-0075172 A | 7/2005 |

* cited by examiner

ELECTRONIC DEVICE AND METHOD FOR PROVIDING EMERGENCY VIDEO CALL SERVICE

CROSS-REFERENCE TO RELATED APPLICATION

This application claims priority under 35 U.S.C. § 119(a) to Korean Application Serial No. 10-2014-0051780, which was filed in the Korean Intellectual Property Office on Apr. 29, 2014, the entire content of which is hereby incorporated by reference.

TECHNICAL FIELD

The present disclosure relates to an electronic device and a method for providing an emergency video call service.

BACKGROUND

As electronic devices have grown in portability and functionality, many are now capable of executing video call services including a voice call between a user and a counterpart user and visual media which is being captured in real-time by an electronic device of the counterpart user.

When the user of the electronic device encounters an emergency situation, the electronic device may provide an emergency voice call through which the user can inform the counterpart user of the emergency situation, and may transmit or receive media images to and from the counterpart user, so as to rapidly respond to the emergency situation.

SUMMARY

Various embodiments of the present disclosure may provide an apparatus and a method for easily securing a witness since, when an emergency situation occurs in the vicinity of a user and the user executes a video emergency call to a particular counterpart recipient, media content (such as an image or a video) related to the emergency may be uploaded in real time and automatically transmitted (e.g., streamed) to other electronic devices located near the user via a streaming network broadcasting channel.

Various embodiments of the present disclosure may provide an apparatus and a method for ensuring the safety of a user. When a user is involved in an emergency and executes a video emergency call to a particular counterpart recipient, the electronic device receiving the video emergency call may transmit an image of the user in addition to locational position information to one or more electronic devices, which may be configured for response to emergency situations.

Various embodiments of the present disclosure may provide an apparatus and a method for efficiently responding to an accident. When a user is in an emergency situation and the user executes a video emergency call to a particular counterpart recipient, accident images and other media images (such as an image or a video) captured from various viewing angles of a plurality of electronic devices situated nearby the user are automatically transmitted to an electronic device which is configured to respond to emergencies.

Various embodiments of the present disclosure may provide an apparatus and a method for preventing an emergency situation from escalating. Voice input from a user caught in the emergency situation is converted into a text form. Thus, voice information of the user is not lost.

Various embodiments of the present disclosure may provide an apparatus and a method for collecting detailed information related to a scene of an accident. A sensor included in the electronic device may be used to detect an environmental condition of the accident scene.

In one aspect of this disclosure, a method of operating an electronic device is disclosed, including: detecting a generation of a specific event, in response to detecting the generation of the event, transmitting a message to one or more other electronic devices located within a predetermined range, and performing communication with the one or more other electronic devices based on requests from the one or more other electronic devices.

In one aspect of this disclosure, a method of operating an electronic device is disclosed, including: receiving a first message from another electronic device, displaying selectable one or more menus for retrieving information related to the another electronic device, and in response to detecting selection of one menu, performing a function specified for the selected menu.

In one aspect of this disclosure, an electronic device is disclosed, including: a communication module, and a process configured to detect the generation of a specific event, control the communication module to transmit a message to one or more other electronic devices located within a predetermined range, and control the communication module to communicate with the one or more other electronic devices based on a request from the one or more second electronic devices.

In one aspect of this disclosure, an electronic device is disclosed, including: a communication module configured to receive a first message from the another electronic device, a display configured to display selectable one or more menus for retrieving information related to the another electronic device, and a processor configured to, in response to detecting selection of one menu, perform a function specified for the selected menu.

BRIEF DESCRIPTION OF THE DRAWINGS

The present disclosure will be more apparent from the following detailed description taken in conjunction with the accompanying drawings, in which.

DETAILED DESCRIPTION

Figure 1:
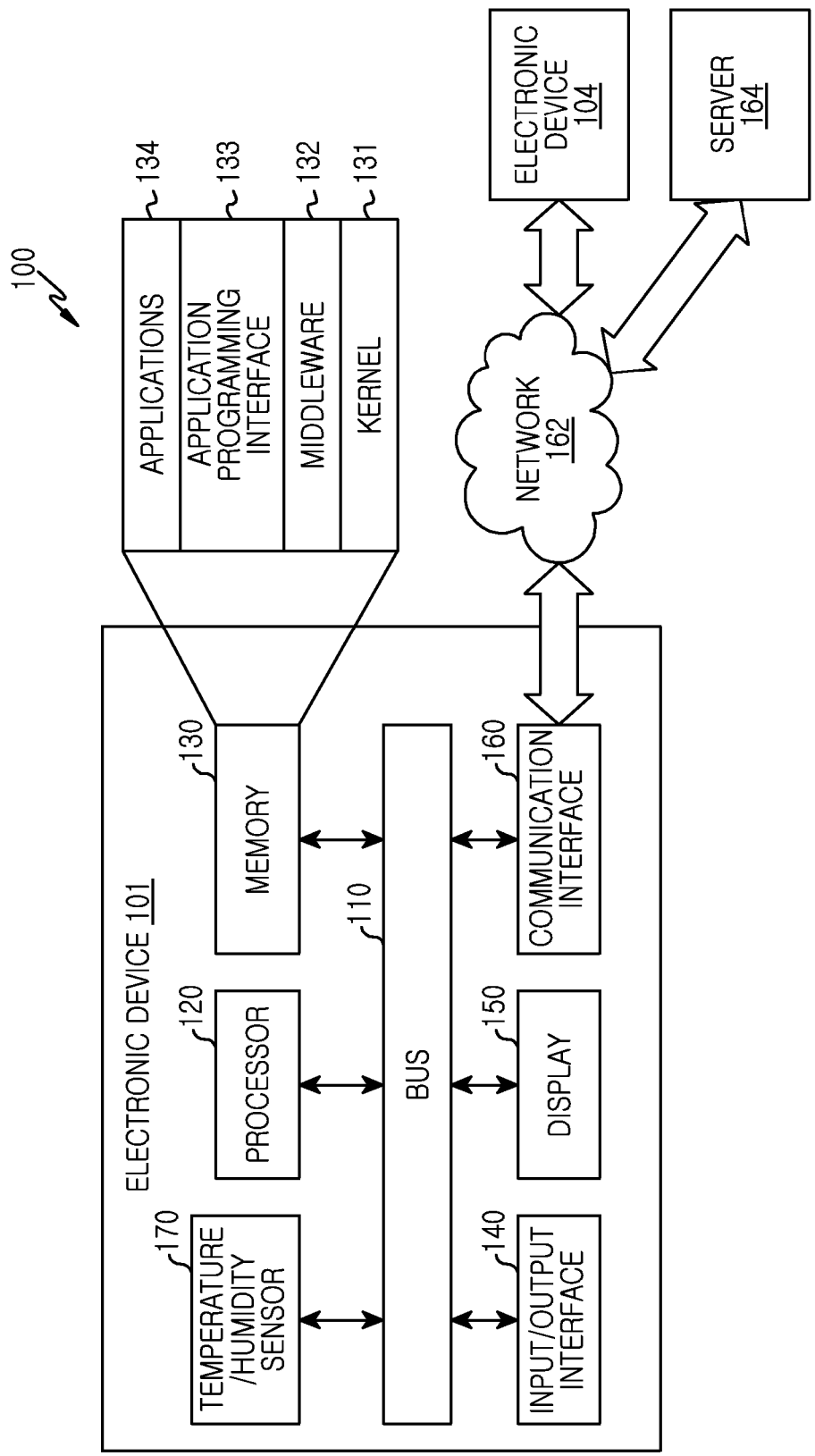
FIG. 1 illustrates a network environment 100 including an example electronic device 101 according to various embodiments.

Hereinafter, the present disclosure will be described with reference to the accompanying drawings. The present disclosure may have various embodiments, and modifications and changes may be made therein. Therefore, the present disclosure will be described in conjunction with particular embodiments shown in the accompanying drawings. However, it should be understood that there is no intent to limit the present disclosure to the particular forms disclosed herein; rather, the present disclosure should be construed to cover all modifications, equivalents, and/or alternatives falling within the ambit of the disclosure. In the description of the drawings, identical or similar reference numerals are used to designate identical or similar elements.

In the present disclosure, the expression "include" or "may include" refers to existence of a corresponding function, operation, or element, and does not limit one or more additional functions, operations, or elements. Also, as used herein, the terms "include" and/or "have" should be construed to denote a certain feature, number, step, operation, element, component or a combination thereof, and should not be construed to exclude the existence or possible addition of one or more other features, numbers, steps, operations, elements, components, or combinations thereof.

Also, as used here, the expression "or" includes any or all combinations of words enumerated together. For example, the expression "A or B" may include A, may include B, or may include both A and B.

In the present disclosure, expressions including ordinal numbers, such as "first" and "second," etc., may modify various elements. However, such elements are not limited by the above expressions. For example, the above expressions do not limit the sequence and/or importance of the corresponding elements. The above expressions may be used merely for the purpose of distinguishing one element from the other elements. For example, a first user device and a second user device indicate different user devices although both of them are user devices. For example, a first element may be termed a second element, and similarly, a second element may be termed a first element without departing from the scope of the present disclosure.

When an element is referred to as being "coupled" or "connected" to any other element, it should be understood that not only the element may be directly coupled or connected to the other element, but also a third element may be interposed therebetween. Contrarily, when an element is referred to as being "directly coupled" or "directly connected" to any other element, it should be understood that no element is interposed therebetween.

The terms used herein are used to describe particular embodiments, and are not intended to limit the present disclosure. As used herein, the singular forms are intended to include the plural forms as well, unless the context clearly indicates otherwise.

Unless defined otherwise, all terms used herein, including technical and scientific terms, have the same meaning as those commonly understood by a person of ordinary skill in the art to which the present disclosure pertains. Such terms as those defined in a generally used dictionary are to be interpreted to have the meaning equal to the contextual meaning in the relevant field of art, and are not to be interpreted to have ideal or excessively formal meaning unless clearly defined in the present disclosure.

An electronic device according to the present disclosure may be a device including a communication function. For example, the electronic device may include at least one of a smartphone, a tablet Personal Computer (PC), a mobile phone, a video phone, an electronic book (e-book) reader, a desktop PC, a laptop PC, a netbook computer, a Personal Digital Assistant (PDA), a Portable Multimedia Player (PMP), an MP3 player, a mobile medical appliance, a camera, and a wearable device (e.g. a Head-Mounted-Device (HMD) such as electronic glasses, electronic clothes, an electronic bracelet, an electronic necklace, an electronic accessory, electronic tattoos, or a smartwatch).

According to some embodiments, the electronic device may be a smart home appliance having a communication function. The smart home appliances may include at least one of, for example, televisions, digital video disk (DVD) players, audio players, refrigerators, air conditioners, cleaners, ovens, microwaves, washing machines, air purifiers, set-top boxes, TV boxes (e.g., HomeSync™ of Samsung, Apple TV™, or Google TV™), game consoles, electronic dictionaries, electronic keys, camcorders, or electronic frames.

According to some embodiments, the electronic device may include at least one of various medical appliances (e.g., magnetic resonance angiography (MRA), magnetic resonance imaging (MRI), computed tomography (CT), and ultrasonic machines), navigation equipment, a global positioning system (GPS) receiver, an event data recorder (EDR), a flight data recorder (FDR), automotive infotainment device, electronic equipment for ships (e.g., ship navigation equipment and a gyrocompass), avionics, security equipment, a vehicle head unit, an industrial or home robot, an automatic teller machine (ATM) of a banking system, or a point of sales (POS) of a shop.

According to some embodiments, the electronic device may include at least one of a part of furniture or a building/structure having a communication function, an electronic board, an electronic signature receiving device, a projector, or various kinds of measuring instruments (e.g., a water meter, an electric meter, a gas meter, a radio wave meter, and the like). The electronic device according to the present disclosure may be a combination of one or more of the aforementioned various devices. Also, the electronic device according to the present disclosure may be a flexible device. Further, it is obvious to those skilled in the art that the electronic device according to the present disclosure is not limited to the aforementioned devices.

Hereinafter, an electronic device according to the various embodiments will be described with reference to the accompanying drawings. In various embodiments, the term "user"

may indicate a person using an electronic device or a device (e.g. an artificial intelligence electronic device) using an electronic device.

FIG. 1 illustrates a network environment 100 including an electronic device 101 according to various embodiments. Referring to FIG. 1, the electronic device 101 may include a bus 110, a processor 120, a memory 130, an input/output interface 140, a display 150, a communication interface 160, and a temperature/humidity sensor 170.

The bus 110 may be a circuit for connecting the aforementioned components and transmitting communication (for example, a control message) between the aforementioned components.

The processor 120 (e.g., may, for example, receive instructions from other components (for example, the memory 130, the input/output interface 140, the display 150, and the communication interface 160) through the bus 110, analyze the received instructions, and execute calculations or data processing according to the analyzed instructions.

The memory 130 may store instructions or data received from or created by the processor 120 or other components (for example, the input/output interface 140, the display 150, the communication interface 160, or the temperature/humidity sensor 170). The memory 130 may include programming modules, for example, a kernel 131, middleware 132, an Application Programming Interface (API) 133, and applications 134. Each of the aforementioned programming modules may be formed of software, firmware, hardware, or a combination of at least two thereof.

The kernel 131 may control or manage system resources (for example, the bus 110, the processor 120, or the memory 130) used for executing an operation or a function implemented in the remaining other programming modules, for example, the middleware 132, or the applications 134. Also, the kernel 131 may provide an interface by which the middleware 132 or the applications 134 access individual components of the electronic device 101 to control or manage the components.

The middleware 132 may serve as a relay so that the applications 134 may communicate with the kernel 131 to exchange data. Furthermore, with regard to task requests received from the applications 134, the middleware 132 may perform a control (for example, scheduling or load balancing) for the task requests, using a method of allocating a priority to at least one of the applications 134 so that the application having the priority can first use the system resources (for example, the bus 110, the processor 120, and the memory 130) of the electronic device 101.

According to various embodiments, the applications 134 may include a Short Message Service (SMS)/Multimedia Messaging Service (MMS) application, an email application, a calendar application, an alarm application, a health care application (for example, an application measuring a quantity of exercise or blood sugar) or an environmental information application (for example, an application providing information on air pressure, humidity or temperature). Additionally or alternately, the applications 134 may include an application related to an information exchange between the electronic device 101 and an external electronic device (for example, an electronic device 104). The application related to the exchange of information may include, for example, a notification relay application for transferring predetermined information to the external electronic device or a device management application for managing the external electronic device.

For example, the notification relay application may include a function of transferring, to the external electronic device (for example, the electronic device 104), notification information generated from other applications of the electronic device 101 (for example, an SMS/MMS application, an e-mail application, a health management application, an environmental information application, and the like). Additionally or alternatively, the notification relay application may receive notification information from, for example, the external electronic device (for example, the electronic device 104) and provide the received notification information to a user. For example, the device management application may manage (for example, install, delete, or update) functions for at least a part of the external electronic device (for example, the electronic device 104) communicating with the electronic device 101 (for example, turning on/off the external electronic device itself (or some elements thereof) or adjusting brightness (or resolution) of a display), applications operating in the external electronic device, or services (for example, a telephone call service or a message service) provided from the external electronic device.

According to various embodiments, the applications 134 may include an application set on the basis of an attribute (for example, the type of electronic device) of the external electronic device (for example, the electronic device 104). For example, when the external electronic device is an MP3 player, the applications 134 may include an application related to the reproduction of music. Similarly, when the external electronic device is a mobile medical device, the applications 134 may include an application related to health care. According to an embodiment, the applications 134 may include at least one of an application designated to the electronic device 101 or an application received from the external electronic device (for example, a server 164 or the electronic device 104).

The input/output interface 140 may transfer instructions or data input from a user through an input/output device (for example, a sensor, a keyboard, or a touch screen) to the processor 120, the memory 130, the communication interface 160, or the temperature/humidity sensor 170 through, for example, the bus 110.

For example, the input/output interface 140 may provide the processor 120 with data for a user's touch input through the touch screen. Furthermore, through the input/output device (for example, a speaker or a display), the input/output interface 140 may output instructions or data received from the processor 120, the memory 130, the communication interface 160, or the temperature/humidity sensor 170 through, for example, the bus 110. For example, the input/output interface 140 may output voice data, which is processed through the processor 120, to a user through a speaker.

The display 150 may display various pieces of information (for example, multimedia data or text data) for the user.

The communication interface 160 may connect communication between the electronic device 101 and the external electronic device (for example, the electronic device 104 or the server 106). For example, the communication interface 160 may be connected to a network 162 through wireless or wired communication to communicate with the external device. The wireless communication may include at least one of, for example, Wi-Fi, Bluetooth (BT), Near Field Communication (NFC), a Global Positioning System (GPS), and cellular communication (for example, Long Term Evolution (LTE), Long Term Evolution-Advanced (LTE-A), Code Division Multiple Access (CDMA), Wideband CDMA (WCDMA), Universal Mobile Telecommunication System (UMTS), Wireless Broadband (WiBro), or Global System for Mobile communication (GSM)). The wired communication may include at least one of, for example, a Universal Serial Bus (USB), a High Definition Multimedia Interface (HDMI), Recommended Standard 232 (RS-232), or a Plain Old Telephone Service (POTS).

Figure 2:
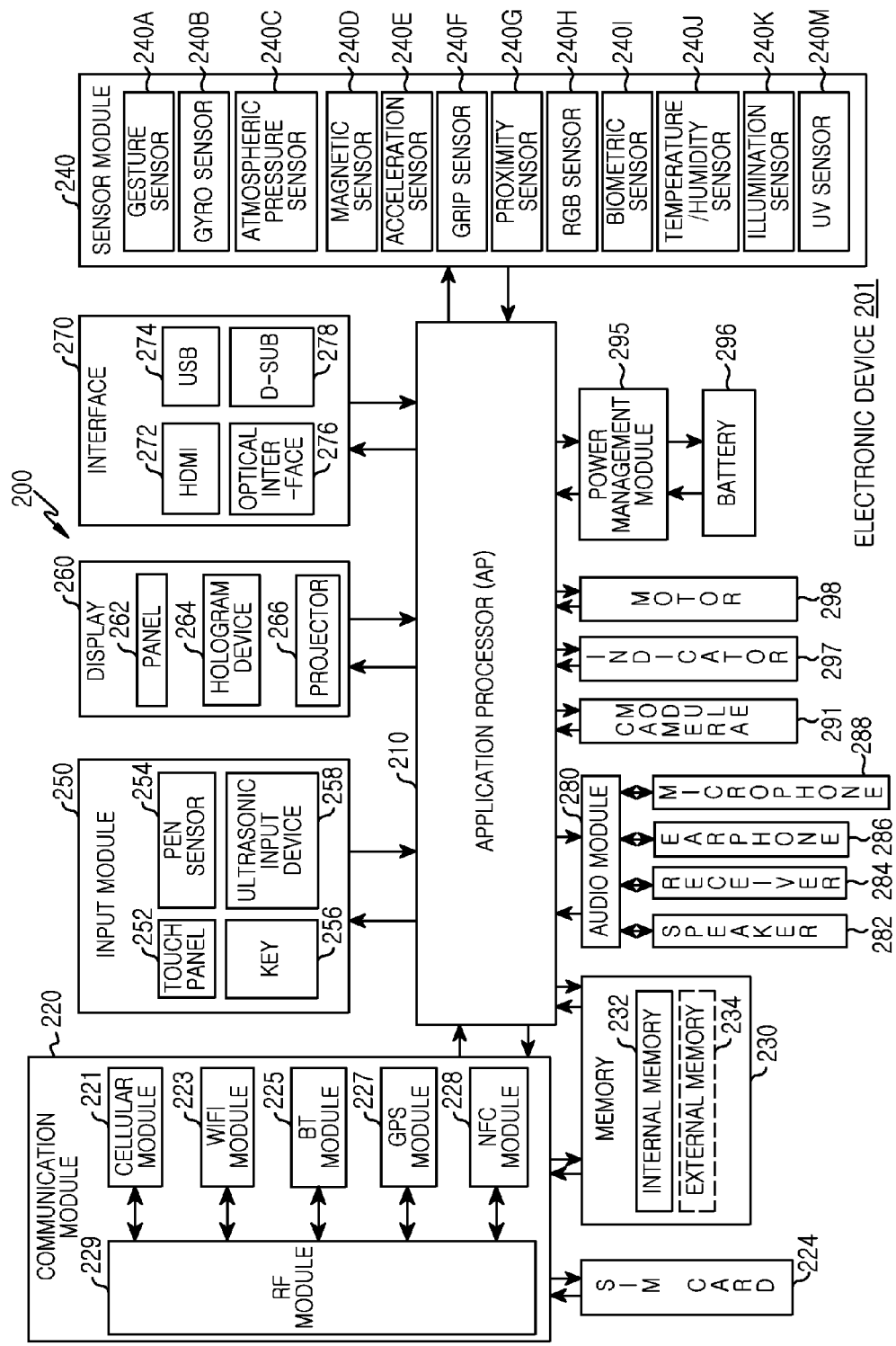
FIG. 2 is a block diagram of example hardware according to various embodiments of the present disclosure.

The temperature/humidity sensor 170 may detect ambient temperature and humidity. FIG. 2 is a block diagram of hardware according to various embodiments. The electronic device 201 may include, for example, all or some of the electronic device 101 illustrated in FIG. 1. The electronic device 201 may include at least one Application Processor (AP) 210, a communication module 220, a Subscriber Identifier Module (SIM) card 224, a memory 230, a sensor module 240, an input device 250, a display 260, an interface 270, an audio module 280, a camera module 291, a power management module 295, a battery 296, an indicator 297, and a motor 298.

The AP 210 may control a plurality of hardware or software components connected to the AP 210 by driving an operating system or an application program and perform processing of various pieces of data including multimedia data and calculations. The AP 210 may be implemented by, for example, a System on Chip (SoC). According to an embodiment, the AP 210 may further include a graphic processing unit (GPU) (not illustrated).

The communication module 220 (for example, the communication interface 160) may perform data transmission/reception in communication between the electronic device 201 (for example, the electronic device 101) and other electronic devices (for example, the electronic device 104 and the server 106) connected thereto through a network. According to an embodiment, the communication module 220 may include a cellular module 221, a Wi-Fi module 223, a BT module 225, a GPS module 227, an NFC module 228, and a Radio Frequency (RF) module 229.

The cellular module 221 may provide a voice call, a video call, a Short Message Service (SMS), or an Internet service through a communication network (for example, LTE, LTE-A, CDMA, WCDMA, UMTS, WiBro, or GSM). Furthermore, the cellular module 221 may distinguish between and authenticate electronic devices within a communication network by using, for example, a subscriber identification module (for example, the SIM card 224). According to one embodiment, the cellular module 221 may perform at least some functions which can be provided by the AP 210. For example, the cellular module 221 may perform at least some of the multimedia control functions.

According to an embodiment, the cellular module 221 may include a communication processor (CP). Furthermore, the cellular module 221 may be implemented by, for example, an SoC. Although the component such as the memory 230 or the power management module 295 is illustrated as a component separated from the AP 210, the AP 210 may include at least some (for example, the cellular module 221) of the components according to an embodiment.

According to an embodiment, the AP 210 or the cellular module 221 (for example, the CP) may load instructions or data received from at least one of a non-volatile memory or other components connected thereto into a volatile memory and process the loaded instructions or data. Furthermore, the AP 210 or the cellular module 221 may store data received from or generated by at least one of other elements in a non-volatile memory.

Each of the Wi-Fi module 223, the BT module 225, the GPS module 227, and the NFC module 228 may include, for example, a processor for processing data transmitted/received through the corresponding module. Although the cellular module 221, the WiFi module 223, the BT module 225, the GPS module 227, and the NFC module 228 are illustrated as separate blocks, at least some (for example, two or more) of the cellular module 221, the WiFi module 223, the BT module 225, the GPS module 227, and the NFC module 228 may be included in one Integrated Chip (IC) or one IC package. For example, at least some (for example, the communication processor corresponding to the cellular module 221 and the WiFi processor corresponding to the WiFi module 223) of the processors corresponding to the cellular module 221, the WiFi module 223, the BT module 225, the GPS module 227, and the NFC module 228 may be implemented as one SoC.

The RF module 229 may transmit/receive data, for example, an RF signal. Although not illustrated, the RF module 229 may include, for example, a transceiver, a Power Amp Module (PAM), a frequency filter, a Low Noise Amplifier (LNA) or the like. Further, the RF module 229 may further include a component for transmitting/receiving electronic waves over a free air space in wireless communication, for example, a conductor, a conducting wire or the like. Although the cellular module 221, the WiFi module 223, the BT module 225, the GPS module 227, and the NFC module 228 share one RF module 829 in FIG. 2, at least one of the cellular module 221, the WiFi module 223 the BT module 225, the GPS module 227, or the NFC module 228 may transmit/receive an RF signal through a separate RF module in one embodiment.

The SIM card 224 may be cards including a subscriber identification module and may be inserted into slots formed on a particular portion of the electronic device. The SIM card may include unique identification information (for example, an Integrated Circuit Card IDentifier (ICCID)) or subscriber information (for example, an International Mobile Subscriber IDentity (IMSI)). Example, the SIM card 224 may include the SIM cards 224_1 to 224_N.

The memory 230 (for example, the memory 130) may include an internal memory 232 or an external memory 234. The internal memory 232 may include, for example, at least one of a volatile memory (for example, a Dynamic RAM (DRAM), a Static RAM (SRAM), and a Synchronous Dynamic RAM (SDRAM)), or a non-volatile Memory (for example, a One Time Programmable ROM (OTPROM), a Programmable ROM (PROM), an Erasable and Programmable ROM (EPROM), an Electrically Erasable and Programmable ROM (EEPROM), a mask ROM, a flash ROM, a NAND flash memory, and an NOR flash memory).

According to an embodiment, the internal memory 232 may be a Solid State Drive (SSD). The external memory 234 may further include a flash drive, for example, a Compact Flash (CF), a Secure Digital (SD), a Micro Secure Digital (Micro-SD), a Mini Secure Digital (Mini-SD), an extreme Digital (xD), a memory stick, or the like. The external memory 234 may be functionally connected with the electronic device 201 through various interfaces. According to an embodiment, the electronic device 201 may further include a storage device (or storage medium) such as a hard drive.

The sensor module 240 may measure a physical quantity or detect an operation state of the electronic device 201, and may convert the measured or detected information to an electrical signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (for example, red, green, and blue (RGB) sensor), a biometric sensor 240I, a temperature/humidity sensor 240J, an illumination sensor 240K, or a Ultra Violet (UV) sensor 240M. Additionally or alternatively, the sensor module 240 may include, for example, an E-nose sensor (not illustrated), an electromyography (EMG) sensor (not illustrated), an electroencephalogram (EEG) sensor (not illustrated), an electrocardiogram (ECG) sensor (not illustrated), an Infrared (IR) sensor, an iris sensor (not illustrated), a fingerprint sensor, and the like. The sensor module 240 may further include a control circuit for controlling one or more sensors included in the sensor module 240.

The input device 250 may include a touch panel 252, a (digital) pen sensor 254, a key 256, or an ultrasonic input device 258. The touch panel 252 may recognize a touch input through at least one of, for example, a capacitive type, a resistive type, an infrared type, and an ultrasonic type. The touch panel 252 may further include a control circuit. The capacitive type touch panel may recognize physical contact or proximity. The touch panel 252 may further include a tactile layer. In this case, the touch panel 252 may provide a tactile reaction to the user.

The (digital) pen sensor 254 may be implemented, for example, using the same or similar method to receiving a user's touch input or using a separate recognition sheet. The key 256 may include, for example, a physical button, an optical key, or a keypad. The ultrasonic input device 258 may identify data by detecting an acoustic wave with a microphone (for example, a microphone 288) of the electronic device 201 through an input unit generating an ultrasonic signal, and may perform wireless recognition. According to an embodiment, the electronic device 201 may also receive a user input from an external device (for example, a computer or a server) connected thereto by using the communication module 220.

The display 260 (for example, the display 150) may include a panel 262, a hologram device 264, or a projector 266. The panel 262 may be, for example, a Liquid Crystal Display (LCD) or an Active Matrix Organic Light Emitting Diode (AM-OLED). The panel 262 may be implemented to be, for example, flexible, transparent, or wearable. The panel 262 may be configured as one module together with the touch panel 252. The hologram device 264 may show a stereoscopic image in the air using interference of light. The projector 266 may project light onto a screen to display an image. The screen may be located, for example, inside or outside the electronic device 201. According to an embodiment, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-subminiature (D-sub) 278. The interface 270 may be included in, for example, the communication interface 160 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280 may bilaterally convert a sound and an electrical signal. At least some components of the audio module 280 may be included in, for example, the input/output interface 140 illustrated in FIG. 1. The audio module 280 may process sound information input or output through, for example, a speaker 282, a receiver 284, earphones 286, the microphone 288 or the like.

The camera module 291 is a device for capturing a still image or a video, and according to an embodiment, may include one or more image sensors (e.g., independent cameras, such as, for example, a front sensor or a rear sensor), a lens (not illustrated), an Image Signal Processor (ISP) (not illustrated), or a flash (not illustrated) (for example, an LED or xenon lamp).

The power management module 295 may manage power of the electronic device 201. Although not illustrated, the power management module 295 may include, for example, a Power Management Integrated Circuit (PMIC), a charger Integrated Circuit (IC), or a battery or fuel gauge.

The PMIC may be mounted to, for example, an integrated circuit or an SoC semiconductor. Charging methods may be classified into a wired charging method and a wireless charging method. The charger IC may charge a battery and prevent over voltage or over current from a charger. According to an embodiment, the charger IC may include a charger IC for at least one of the wired charging or the wireless charging. Examples of the wireless charging method may include a magnetic resonance type, a magnetic induction type, or an electromagnetic wave type, and an additional circuit for wireless charging, such as a coil loop circuit, a resonance circuit, or a rectifier circuit may be added.

The battery gauge may measure, for example, a remaining quantity of the battery 296, or a voltage, a current, or a temperature during the charging. The battery 296 may store or generate electricity, and may supply power to the electronic device 201 using the stored or generated electricity. The battery 296 may include, for example, a rechargeable battery or a solar battery.

The indicator 297 may display a specific status of the electronic device 201 or the part (for example, the AP 210) of electronic device 201, for example, a booting status, a message status, a charging status, and the like. The motor 298 may convert an electrical signal to a mechanical vibration. Although not illustrated, the electronic device 201 may include a processing unit (for example, a GPU) for supporting mobile TV. The processing unit for supporting mobile TV may process media data according to a standard of Digital Multimedia Broadcasting (DMB), Digital Video Broadcasting (DVB), media flow or the like.

Each of the components of the electronic device according to the present disclosure may be implemented by one or more components and the name of the corresponding component may vary depending on the type of the electronic device. The electronic device according to the present disclosure may be configured by including at least one of the above-described elements, and some of the elements may be omitted, or other elements may be added. Further, some of the elements of the electronic device according to the present disclosure may be combined to be one entity, which can perform the same functions as those of the components before the combination.

The term "module" used in the present disclosure may refer to, for example, a unit including one or more combinations of hardware, software, and firmware. The "module" may be interchangeably used with a term, such as unit, logic, logical block, component, or circuit. The "module" may be the smallest unit of an integrated component or a part thereof. The "module" may be the smallest unit that performs one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), or a programmable-logic device for performing operations which has been known or are to be developed hereinafter.

According to various embodiments of the present disclosure, a first electronic device may include: a process for detecting the generation of a specific event; and a communication module for detecting the event, transmitting a predetermined message to one or more second electronic devices located within a predetermined range, and communicating with the one or more second electronic devices according to a request from the one or more second electronic devices.

The specific event may be an event for detecting a start of a streaming service.

The specific event may be an event for detecting transmission of an emergency call.

The specific event may be an event for detecting that a user's heart rate received from another linked electronic device is larger than or equal to or equal or smaller than a predetermined heart rate.

The specific event may be an event for detecting that an ambient temperature sensed using at least one arranged sensor is higher than or equal to a predetermined temperature.

The communication module may enable an arranged wireless communication module and transmit the predetermined message to the one or more second electronic devices.

The wireless communication module may be at least one of BLE, WiFi, or Bluetooth modules.

The communication module may enable an arranged wireless communication module.

The message may include an ID of the first electronic device and a Bluetooth Media Access Control (MAC) address or WiFi Service Set IDentifier (SSID) information of the first electronic device.

When a request for position identification information is received from the one or more second electronic devices, the communication module may transmit current position information to the one or more second electronic devices.

When a request for a video emergency call (ex. video telephony emergency call) is received from the one or more second electronic devices, the processor may add the one or more second electronic devices as counterparts in the video emergency call.

The first electronic device may identify that the video emergency call switches to a video emergency conference call.

When a request for receiving an image is received from the one or more second electronic devices, the communication module may transmit image data photographed in real time to the one or more second electronic devices.

According to various embodiments of the present disclosure, a second electronic device located within a predetermined range from a first electronic device includes: a communication module for receiving a first message from the first electronic device; a display for displaying a window including one or more menus by which information on the first electronic device can be identified; and a processor for, when one of the one or more menus is selected, performing a function specified for the selected menu.

The communication module may receive an ID of the first electronic device and a Bluetooth Media Access Control (MAC) address or WiFi Service Set IDentifier (SSID) information of the first electronic device, enable an arranged wireless communication module by receiving the information, and receive a second message corresponding to an emergency message when the first electronic device is discovered.

The one or more menus include at least one of a position identification menu for identifying a position of the second electronic device, a video emergency call join menu for performing a video emergency call with the first electronic device, or an image reception menu for accessing an Internet broadcasting channel established by the first electronic device and displaying in real time an image photographed by the first electronic device.

When a video emergency call join menu for performing a video emergency call with the first electronic device is selected from the one or more menus, the communication module may transmit image data photographed using an arranged camera module to one or more third electronic devices which deal with accidents.

According to various embodiments of the present disclosure, an electronic device is disclosed, including: a communication interface for communicating over a network, a plurality of cameras for capturing images (such as an image or a video), and a controller configured to control operations of establishing connections with at least a first external device and a second external device via the communication interface in response to detecting execution of an emergency call, executing the emergency call with the first external device, and transmitting images captured by the plurality of cameras to the second external device for streaming.

According to various embodiments of the present disclosure, an electronic device is disclosed, including: a communication interface for communicating over a network, and a controller configured to control operations of: in response to receiving an emergency message from an external device, displaying selectable options for retrieving information related to the emergency message from the external device, and in response to detecting selection of one of the options, transmitting a corresponding request to the external device.

Figure 3:
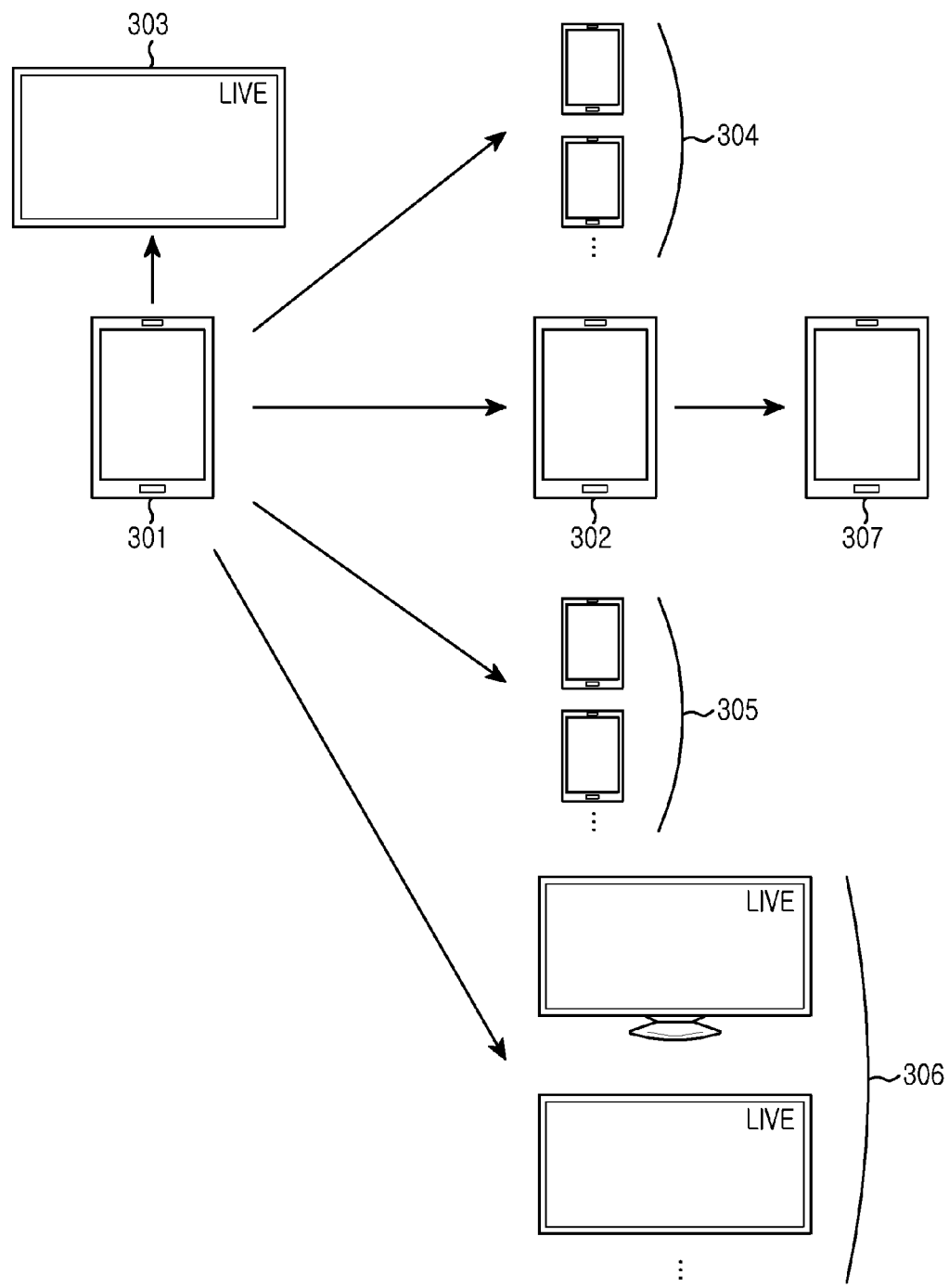
FIG. 3 illustrates overall configurations of an example first through fifth electronic device according to various embodiments of the present disclosure.

FIG. 3 illustrates example configurations of a first through a fifth electronic device according to various embodiments of the present disclosure. A first electronic device 301 may first make a request for a video emergency call to a second electronic device 302. For example, when a user of the first electronic device 301 encounters an emergency situation such as a fire, a traffic accident or the like, the user of the first electronic device 301 may make a request for the video emergency call to the second electronic device 302 in order to request emergency aid or rescue from a user (such as a receptionist at an emergency response facility) of the second electronic device 302.

According to various embodiments, when the first electronic device 301 detects the request for the video emergency call transmitted to the second electronic device 302, the first electronic device 301 may establish a streaming service 303 to inform not only the user of the second electronic device 302, but also users of other electronic devices 304 and 305 and another device 306 of the scene of the accident which transpired in the vicinity or proximity of the user of the first electronic device 301.

According to various embodiments, the first electronic device 301 may upload image (or video) data captured with a camera module of the first electronic device 301 to the established streaming service 303 in real-time. Further, the first electronic device 301 may perform the following operations. Hereinafter, the operations of the first electronic device 301 will be sequentially described. All the operations may be performed at the same time, or performed according to priorities different than the following operation sequences.

The first electronic device 301, having established the streaming service 303, may transmit information related to the established streaming service 303 (e.g., connection information) to the second electronic device 302, which has received the request for the voice emergency call. For example, the first electronic device 301 may transmit Uniform Resource Locator (URL) information of the streaming service 303 to the second electronic device 302 which has received the request for the voice emergency call.

Simultaneously or sequentially, the first electronic device 301 may transmit the information related to the established streaming service 303 to at least one third electronic device 304. The third electronic device 304 may be an electronic device designated to automatically transmit the information related to the established streaming service 303 when an emergency situation is experienced or encountered by the user of the first electronic device 301. For example, the third electronic device 304 may be an electronic device of families, relatives, and close friends of the user of the first electronic device 301. According to an embodiment, the first electronic device 301 may use a phone number list of the third electronic device 304 stored in the first electronic device 301, or use a phone number list of the third electronic device 304 stored in an external server. Simultaneously or sequentially, the first electronic device 301 may transmit a specific emergency message to at least one fourth electronic device 305 located within a predetermined range. The message transmitted by the first electronic device may include an emergency message which the first electronic device broadcasts by using short-range communication such as BLE and WiFi, as well as other longer range methods, such as transmission through a base station. Hereinafter, even if a separate message sentence is not stated, the message transmitted by the first electronic device may include an emergency message, which the first electronic device broadcasts by using short-range communication such as BLE and WiFi, as well as other longer range methods, such as transmission through a base station. The fourth electronic device 305 may be an electronic device located within a predetermined range from the first electronic device 301. For example, the fourth electronic device 305 may be an electronic device camped on the same base station as the first electronic device 301 (transmission then being cellular). More specifically, the first electronic device 301 may transmit a specific message such as "An accident has happened. I need help" to all fourth electronic devices 305 camped upon the same base station as the first electronic device 301.

According to various embodiments, when the first electronic device 301 detects the generation of a specific event, the first electronic device 301 may enable a short-range communication module and transmit an emergency message through the short-range communication module or a cellular network. According to an embodiment, when the first electronic device 301 transmits the emergency message through the cellular network, the electronic device 301 may transmit the emergency message to the fourth electronic device 305. According to an embodiment, the aforementioned cellular network may be a WiFi network.

According to various embodiments, the specific event detected by the first electronic device 301 may be an event for detecting the start of a streaming service, an event for detecting the transmission of an emergency call, an event for detecting that a user's heart rate received from another electronic device is larger than or equal to or equal to or smaller than a predetermined heart rate (e.g., equaling or exceeding a minimum or a maximum heart rate threshold), or an event for detecting that an ambient temperature sensed using at least one sensor is higher than or equal to a predetermined temperature.

Simultaneously or sequentially, the first electronic device 301 may transmit image data which is photographed in real time to at least one predetermined device 306. The predetermined device 306 may be a device such as an Internet Protocol Television (IP TV) or a Personal Computer (PC). For example, the first electronic device 301 may transmit image data associated with a scene of an accident which happened to the user of the first electronic device 301 to an IP TV and a PC installed at a home of the user of the electronic device 301. Accordingly, at least one device 306 having received the image data from the first electronic device 301 may display the image data. Simultaneously or sequentially, the second electronic device 302 may add at least one fifth electronic device 307 serving to process the accident as a counterpart of the video emergency call. Accordingly, the first electronic device 301 may identify that the video emergency call switches to a video emergency conference call as the fifth electronic device 307 is added as the counterpart of the video emergency call. The fifth electronic device 307 may be an electronic device used by a user who deals with accidents in a police station, fire station, and hospital.

Simultaneously or sequentially, the second electronic device 302 may transmit Internet address information received from the first electronic device 301 to the fifth electronic device 307 simultaneously with the addition of at least one fifth electronic device 307 as the counterpart of the video emergency call. Accordingly, the fifth electronic device 307 performing the accident processing may access the received Internet address to identify an emergency situation which the user of the first electronic device 301 encounters.

According to various embodiments, the message transmitted to at least one fourth electronic device 305 located within a predetermined range by the first electronic device 301 may be a trigger message for enabling a communication module of the fourth electronic device 305. According to an embodiment, the message transmitted to at least one fourth electronic device 305 located within the predetermined range by the first electronic device 301 may include an ID of the first electronic device 301 and information on a communication module to be used.

According to an embodiment, when the first electronic device 301 performs short-range communication with at least one fourth electronic device 305 through Bluetooth, the message transmitted to the fourth electronic device 305 by the first electronic device 301 may include an ID of the first electronic device 301 and a Bluetooth Media Access Control (MAC) address of the first electronic device 301.

According to an embodiment, when the first electronic device 301 performs short-range communication with at least one fourth electronic device 305 through WiFi, the message transmitted to the fourth electronic device 305 by the first electronic device 301 may include an ID of the first electronic device 301 and WiFi Service Set Identifier (SSID) information of the first electronic device 301.

According to various embodiments, when the fourth electronic device 305 receives a trigger message from the first electronic device, the fourth electronic device 305 may enable a short-range communication module such as BT, BLE, or WiFi. According to an embodiment, the fourth electronic device 305 may identify the ID of the first electronic device 301 and the communication module to be used, included in the trigger message to search for the first electronic device 301.

According to various embodiments, when the fourth electronic device 305 discovers the first electronic device 301, the fourth electronic device 305 may receive an emergency message from the first electronic device 301. According to an embodiment, the fourth electronic device 305 may be connected to the first electronic device 301 to receive the emergency message, or the emergency message may be included in a broadcast or beacon signal transmitted by the first electronic device 301 before the fourth electronic device 305 is connected to the first electronic device 301.

According to various embodiments, when the fourth electronic device 305 searches for the first electronic device 301 but has not discovered the first electronic device 301, the fourth electronic device 305 may periodically search for the first electronic device 301 after a predetermined time. According to an embodiment, when the fourth electronic device 305 has not discovered the first electronic device 301 even though the fourth electronic device 305 searches for the first electronic device 301 on a predetermined cycle, the fourth electronic device 305 may turn off the enabled communication module.

Figure 4A:
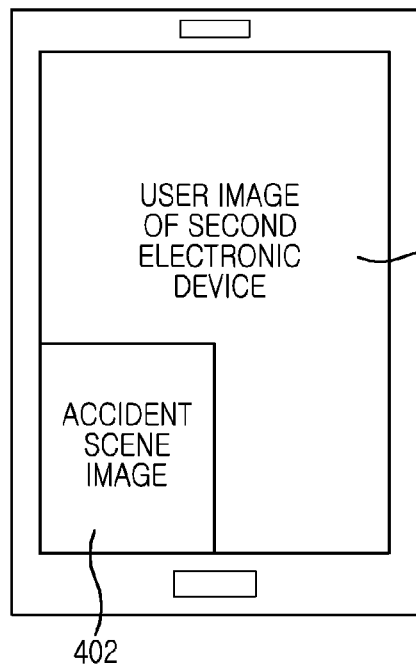
FIG. 4A, FIG. 4B and FIG. 4C illustrate example screens displayed on a first electronic device to a third electronic device according to various embodiments of the present disclosure.
Figure 4B:
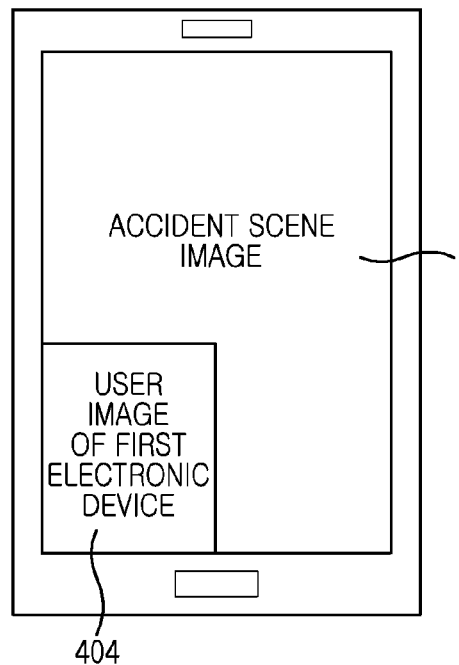
Figure 4C:
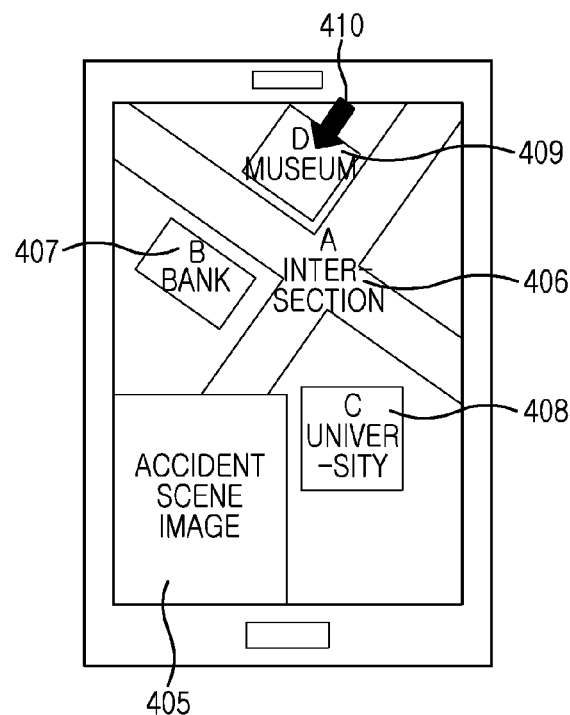

FIG. 4A, FIG. 4B and FIG. 4C illustrate example screens displayed on the first through third electronic device according to various embodiments of the present disclosure. When the first electronic device detects a request for a video emergency call transmitted to the second electronic device, the first electronic device may establish an Internet broadcasting channel.

According to various embodiments, the first electronic device may update an image photographed using a camera module included in the first electronic device to the established streaming service in real time.

According to various embodiments, when a video emergency call is connected between the first electronic device and the second electronic device, the first electronic device may display a user image of the second electronic device and an accident scene image in predetermined areas of a display of the first electronic device.

For example, as illustrated in FIG. 4A, the first electronic device may display an accident image captured by the first electronic device in a lower area 402 of the display and an image of a user of the second electronic device, who is a counterpart user in a video emergency call in the remaining area 401 of the display. Hereinafter, an embodiment of a screen display method of the second electronic device corresponding to the counterpart of the first electronic device in the video emergency call will be described.

The second electronic device having received a request for a video emergency call from the first electronic device may execute the video emergency call with the first electronic device. For example, when the second electronic device receives the request for the video emergency call from the first electronic device, the second electronic device may receive an input from the user of the second electronic device confirming execution of the requested video emergency call.

According to various embodiments, when the video emergency call is connected between the first electronic device and the second electronic device, the second electronic device may display an image and/or video of the other user and an accident scene image, both captured by the first electronic device. The respective images may be displayed in predetermined areas of a display of the second electronic device.

For example, as illustrated in FIG. 4B, the second electronic device may display the user image of the first electronic device in a lower area 404 of the display (e.g., as captured by a first image sensor of the camera module). The second electronic device may also display an emergency video or image of an accident scene, as captured and transmitted by the first electronic device in the remaining area 403 of the display (e.g., as captured by a second image sensor of the camera module). Hereinafter, an embodiment of a screen display method of the third electronic device when the third electronic device is added as the counterpart of the video emergency call after the video emergency call is connected between the first electronic device and the second electronic device will be described.

The third electronic device may receive a request for joining the video emergency call from the second electronic device and may join the video emergency call as another counterpart user. The third electronic device may be used by a user who deals with accidents in, for example, a police station, fire station, or a hospital.

After detecting that the video emergency call has switched to a video emergency conference call including the third electronic device, the third electronic device may display the image or video captured and transmitted from the first electronic device, and geographic position information of the first electronic device. This information may be displayed in predetermined areas of a display of the third electronic device.

For example, as illustrated in FIG. 4C, the third electronic device may display the user image of the first electronic device in a lower area 405 of the display, and detailed position information of the first electronic device in the remaining areas of the display. More specifically, for example, a firefighter who is the user of the third electronic device may identify that the user of the first electronic device is currently located in "D museum 410," situated near "B bank 407" and "C university 408" situated at "A intersection 406," through a visual icon 410 displayed while the user moves towards the site.

Figure 5A:
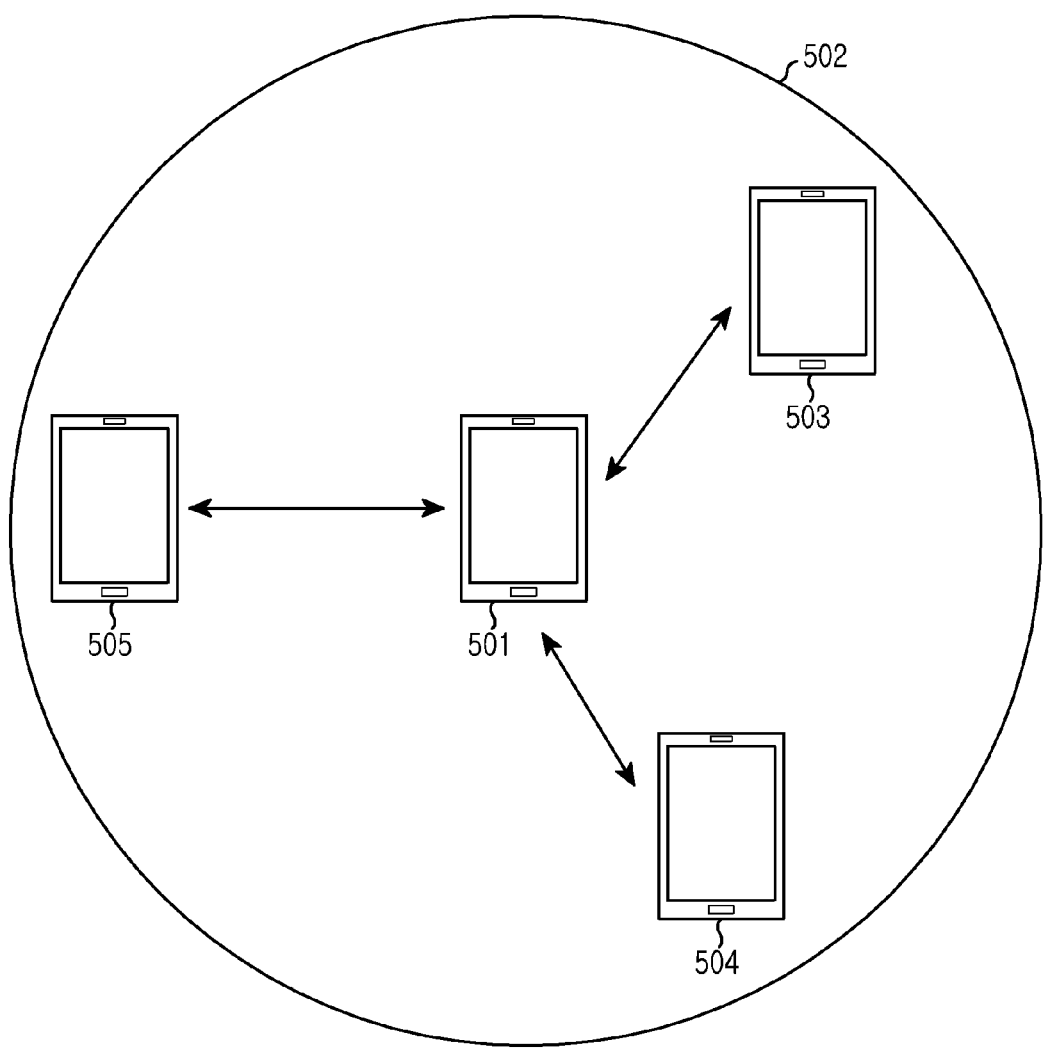
FIG. 5A and FIG. 5B illustrate an example wireless communication method between a first electronic device and second electronic devices located within a predetermined range from the first electronic device according to various embodiments of the present disclosure.
Figure 5B:
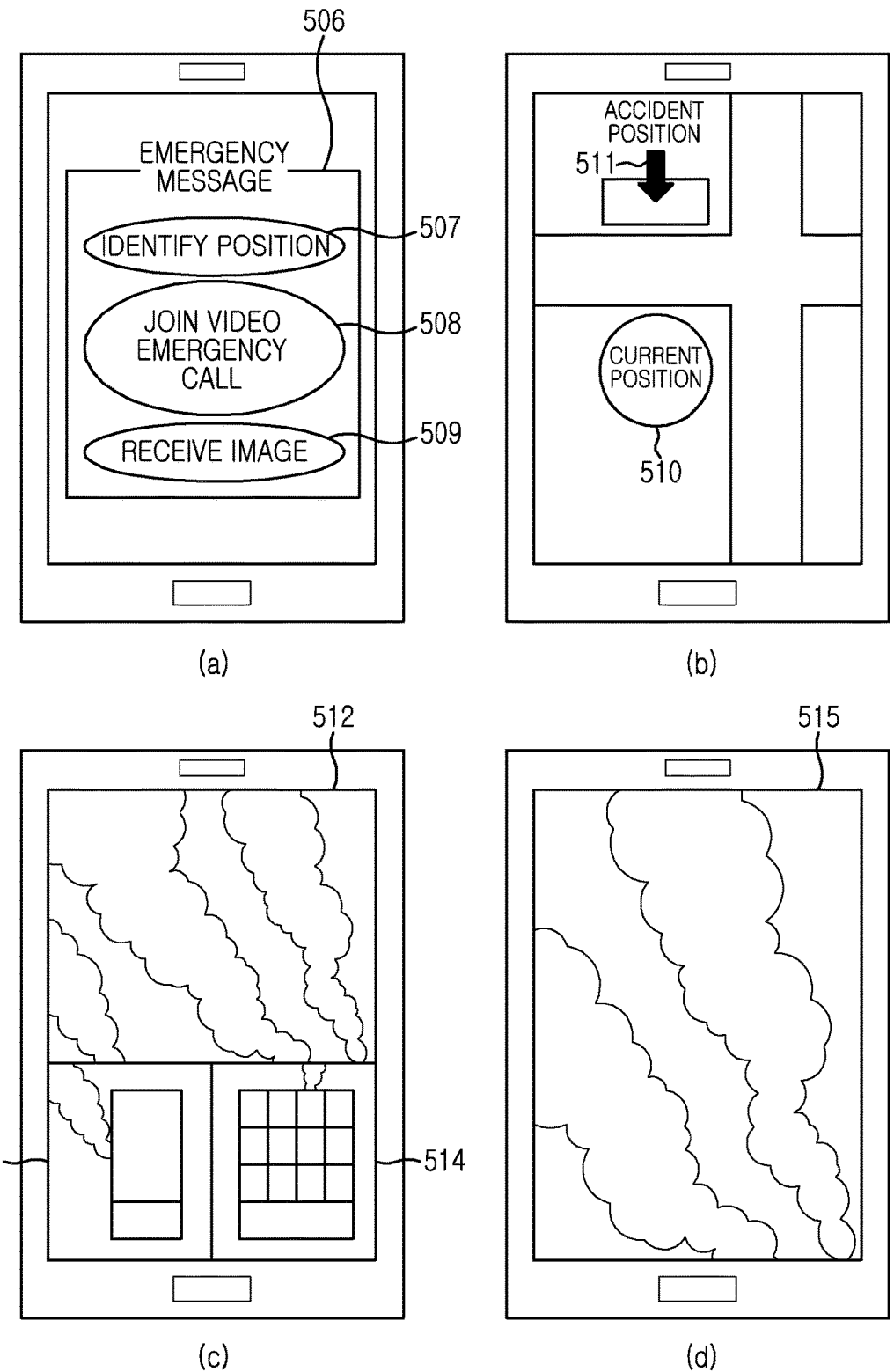

FIG. 5A and FIG. 5B illustrate a wireless communication method between the first electronic device and second electronic device located within a predetermined range from the first electronic device according to various embodiments. Hereinafter, the first electronic device is defined as an electronic device of a user in an emergency situation, and the second electronic device is defined as an electronic device located within a predetermined range from the first electronic device. Further, a message transmitted by the first electronic device may include an emergency message which the first electronic device broadcasts by using short-range communication such as BLE as well as a method through a base station. Hereinafter, even if a separate sentence is not stated, the message transmitted by the first electronic device may include the emergency message which the first electronic device broadcasts by using short-range communication such as BLE as well as the method through the base station. According to various embodiments, the first electronic device may transmit a specific emergency message to at least one second electronic device within a predetermined range from the first electronic device. For example, as illustrated in FIG. 5A, the first electronic device 501 may transmit emergency messages requesting aid to one or more second electronic devices 503, 504, and 505, the second electronic devices 503, 504, and 505 being camped on the same cell 502 as the first electronic device 501.

According to various embodiments, the first electronic device and the one or more second electronic devices, having received the specific emergency messages from the first electronic device, may enable wireless communication modules included therein. For example, as illustrated in FIG. 5A, in order to perform communication between the first electronic device 501, and the second electronic devices 503, 504, and 505, the first electronic device 501 and the second electronic devices 503, 504, and 505 may enable at least one of the wireless short-range communication modules such as WiFi modules and Bluetooth modules included therein.

According to various embodiments, the one or more second electronic devices may display a window including one or more menus for identifying information on the second electronic devices. The one or more menus may include at least one of a position identification menu for identifying a position of the first electronic device, a video emergency call join menu for performing a video emergency call with the first electronic device, and an image reception menu for accessing a streaming service established by the first electronic device and displaying an image photographed by the first electronic device in real time.

For example, as illustrated in FIG. 5B, diagram (a), an emergency message 506 displayed on a display of the second electronic device may include menus (e.g., buttons, icons, controls, functions) such as a position identification menu 507 (e.g., "identify position"), a video emergency call menu 508 (e.g., "join video emergency call"), and an image reception menu 509 (e.g., "receive image," which may indicate capturing or taking a photograph or video).

According to various embodiments, the one or more second electronic devices may perform each of the designated functions for each of the menus in response to detecting selection of one of the menus included in the displayed window. For example, as illustrated in FIG. 5B, diagram (b), when the user selects the "identify position menu" from the menus displayed on the second electronic device, the second electronic device may display information indicating a current position 510, and an accident position 511 (via an icon or indicator) which illustrates the position of the first electronic device on the display.

In another example, as illustrated in FIG. 5B, diagram (c), when the user selects the "video emergency call join menu" from the menus displayed on the second electronic device, the second electronic device may be added as a counterpart of the first electronic device in the video emergency call. For example, the second electronic device may display images, which are being captured or photographed by users who join the video emergency call, in a lower left area 513, a lower right area 514, and the remaining area (or areas) 512 of the display of the second electronic device, respectively.

In still another example, as illustrated in FIG. 5B, element (d), when the user selects the "receive image" menu from the menus displayed on the second electronic device, the second electronic device may receive the image captured by the first electronic device from the first electronic device and display the received image in a predetermined area 515. Moreover, the second electronic device may transmit an image or video of the accident scene captured from a viewing angle of the second electronic device to the first electronic device, or may receive an image or video of the accident scene captured by the first electronic device from the first electronic device. For example, the second electronic device may receive and display an image captured from a viewing angle of the first electronic device. The image may be displayed in a display 515 of the second electronic device.

FIG. 6A, FIG. 6B, FIG. 6C and FIG. 6D illustrate screens displayed on the first electronic device according to various embodiments. In the following description, a first electronic device will be defined as an electronic device used by a user who is in charge of dealing with accidents, a second electronic device will be defined as an electronic device which joins an initial video emergency call with the first electronic device, a third electronic device will be defined as an electronic device which makes a request for a video emergency call to the second electronic device, and a fourth electronic device will be defined as an electronic device which is located within a predetermined range from the third electronic device.

According to various embodiments, the first electronic device may receive a request for joining a video emergency call from the second electronic device. Then, the first electronic device may join the requested video emergency call and receive information related to a streaming service established by the third electronic device from the second electronic device at the same time.

Figure 6A:
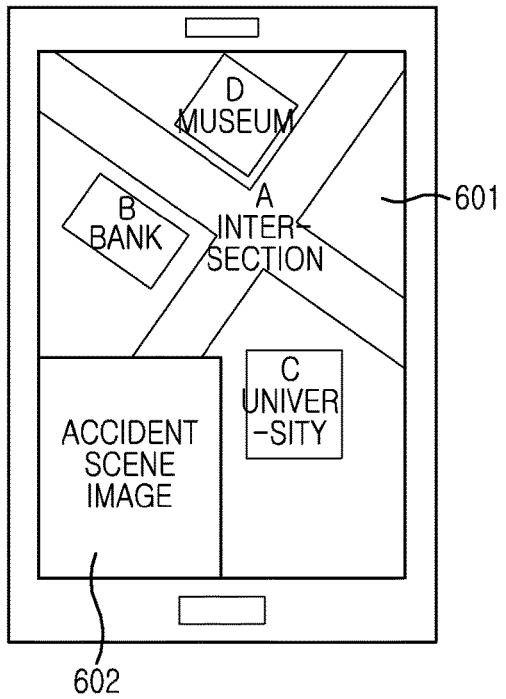
FIG. 6A, FIG. 6B, FIG. 6C and FIG. 6D illustrate example screens displayed on a first electronic device according to various embodiments of the present disclosure.

According to various embodiments, the first electronic device may access a streaming service established by the second electronic device and display an image photographed by the first electronic device and position information of the first electronic device in predetermined areas of a display of the first electronic device. For example, as illustrated in FIG. 6A, the first electronic device may display an image photographed at a position of the first electronic device in the lower right area 602 and position information of the first electronic device in the remaining area 601.

Figure 6B:
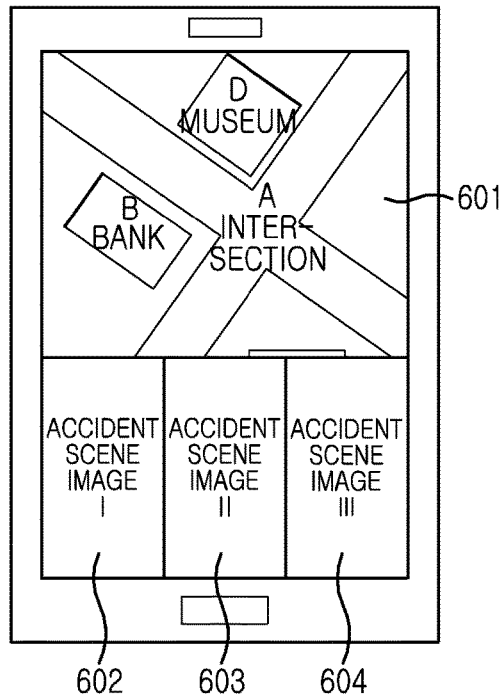

According to various embodiments, the first electronic device may receive images photographed at respective positions by one or more fourth electronic devices located within a predetermined range from the third electronic device, and display the received images in predetermined display areas. For example, as illustrated in FIG. 6B, description will be made for a case where the first electronic device receives images photographed at respective positions by three fourth electronic devices (e.g. 305 of FIG. 3) will be described.

In the above described example, the first electronic device may display images photographed at respective positions by the fourth electronic devices in predetermined areas 602, 603, and 604 of the display of the first electronic device. Further, the first electronic device may also display position information of the first electronic device in the remaining display areas 601. That is, since the first electronic device may receive in real time images photographed at various positions by electronic devices of users, police officers, firefighters, and agents who perform emergency treatment may effectively prepare for emergency situations.

According to various embodiments, the first electronic device may determine which images will be displayed at predetermined display areas by determining positions of the fourth electronic devices. According to an embodiment, when fourth electronic device #1 captures photography on a leftwards side of the accident site, fourth electronic device #2 captures photography at a frontwards side of the accident site, and fourth electronic device #3 captures photography on a rightwards side of the accident site, the first electronic device may display an image photographed by fourth electronic device #1 in the area 602, an image photographed by fourth electronic device #3 in the area 603, and an image photographed by fourth electronic device #2 in the area 604, corresponding to their real-world geographic positioning.

Figure 6C:
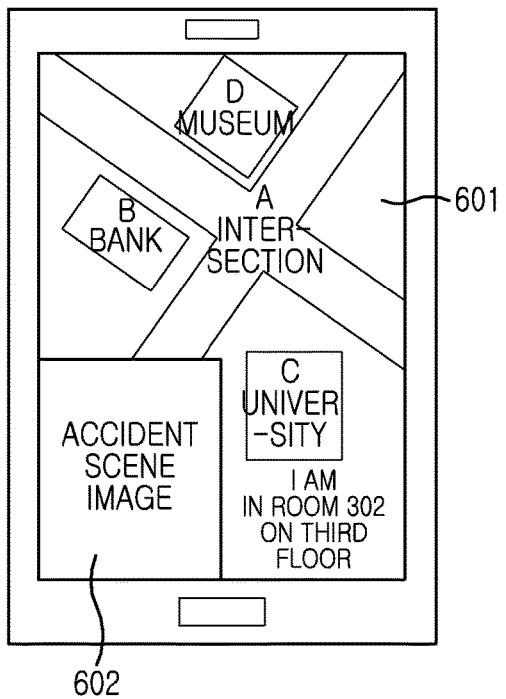

According to various embodiments, the first electronic device may also display text information generated by converting voice information of the user of the first electronic device and another user joining the voice emergency call into a text form. For example, as illustrated in FIG. 6C, since each of the electronic devices joining the video emergency call may convert voice information of users of the electronic devices into a text form through a Speech To Text (STT) function, the voice of each user may be identified in text form in emergency situations.

According to an embodiment, in the predetermined area 602 of the first electronic device used by a firefighter who is moving to an accident scene, a voice of the user of the third electronic device located in the accident scene may be shown in the text form such as "I am in room 303 on the third floor now."

Figure 6D:
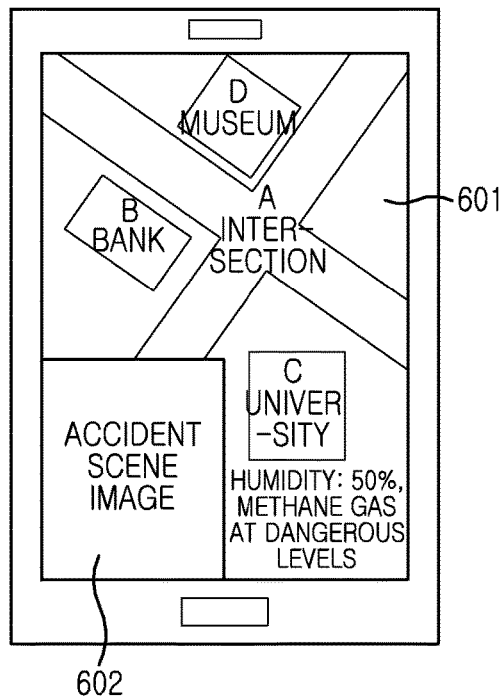

According to an embodiment, text information generated by converting voice information of the user of the first electronic device and other users joining the video emergency call into the text form may be shown through scrolling. For example, the user of the first electronic device may scroll a screen of the first electronic device to view previous conversation contents in the text information converted into the text form which are not displayed on the screen. According to various embodiments, the first electronic device may also display humidity information and information on components of atmosphere detected by the third electronic device in a predetermined area of the display of the first electronic device. For example, as illustrated in FIG. 6D, the first electronic device may also display, in a lower left area 602 of the first electronic device, information indicating environmental conditions, such as "humidity: 50%" and other related information such as "methane gas at dangerous levels," as detected by the third electronic device in the accident scene. According to an embodiment, the third electronic device may transmit various pieces of information detected by the third electronic device to the first electronic device and inform of the information in various ways. In the above described example, the first electronic device may display humidity information and information on components of atmosphere in the site, and may inform the user of the first electronic device of the information in various ways such as a voice, vibration or the like.

Figure 7:
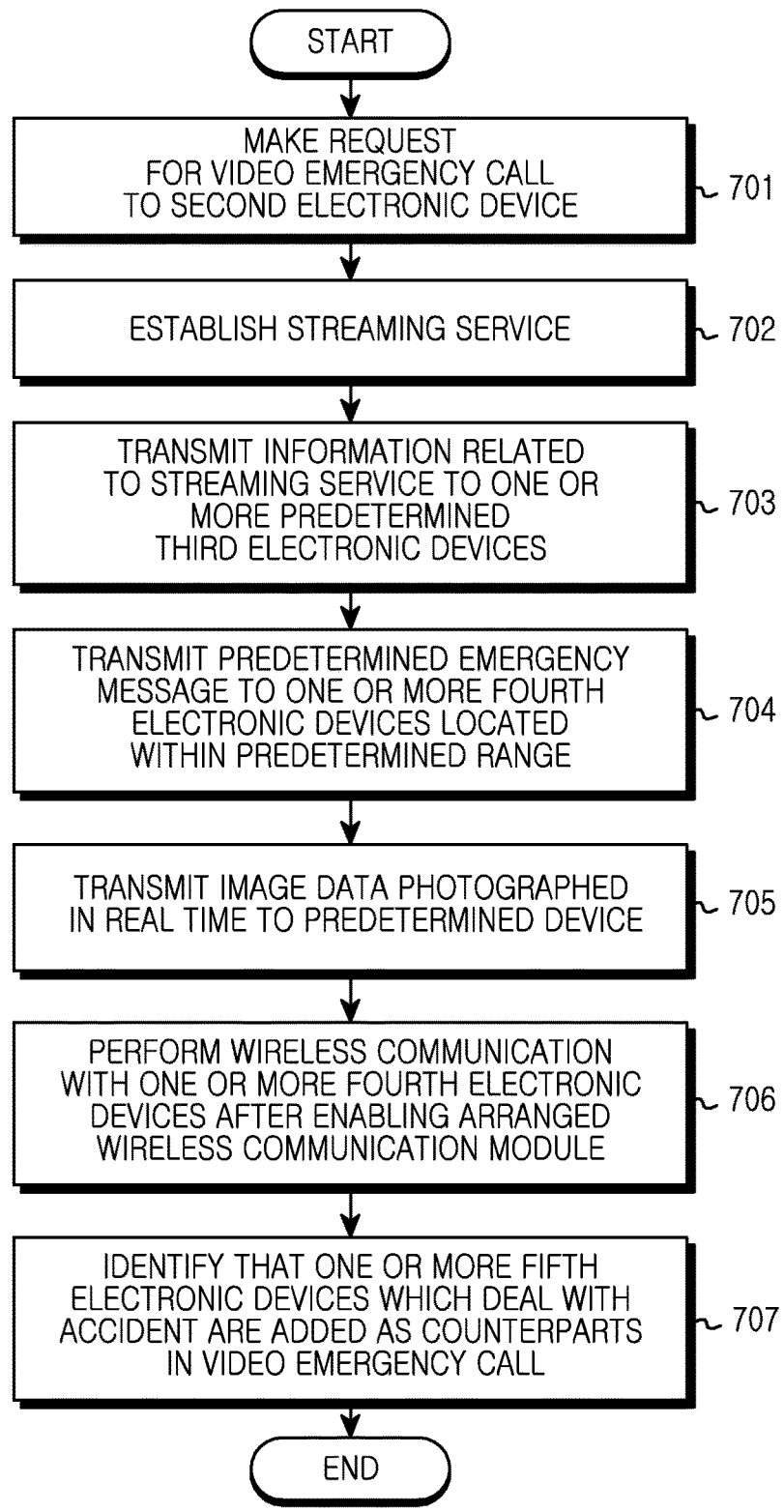
FIG. 7 is a flowchart illustrating an example process performed by a first electronic device of a user in an emergency situation according to various embodiments of the present disclosure.

FIG. 7 is a flowchart illustrating an example process performed by a first electronic device of the user in an emergency situation according to various embodiments of the present disclosure. In the following description, a second electronic device will be defined as an electronic device which receives a request for an initial video emergency call from the first electronic device, third electronic devices will be defined as one or more predetermined electronic devices, a fourth electronic device will be defined as an electronic device which is located within a predetermined range from the first electronic device, and a fifth electronic device will be defined as an electronic device of a user who is in charge of dealing with accidents.

In step 701, the first electronic device may make a request for a video emergency call to the second electronic device. For example, in an emergency situation, the first electronic device may make the request for the video emergency call to connect a video call with the user of the second electronic device.

In operation 702, the first electronic device may establish a streaming service. For example, when the first electronic device detects a request for a video emergency call transmitted to the second electronic device, the first electronic device may upload, in real time, a scene image photographed at a position of the first electronic device.

In operation 703, the first electronic device may transmit information related to the established streaming service to one or more predetermined third electronic devices. For example, the first electronic device may transmit URL information of the established streaming service to one or more third electronic devices which are electronic devices used by families, relatives, and close friends of the user of the first electronic device.

In operation 704, the first electronic device may transmit an emergency message to one or more fourth electronic devices located within a predetermined range. For example, the first electronic device may transmit an emergency message such as "There is an emergency. Please help." to one or more fourth electronic devices located in the same base station as that including the first electronic device.

In operation 705, the first electronic device may transmit image data photographed in real time to a predetermined device. For example, the first electronic device may transmit image data associated with a scene of an accident which happened to the user of the first electronic device to an IP TV and a PC installed at home of the first electronic device.

In operation 706, after enabling a wireless communication module included in the first electronic device, the first electronic device may perform wireless communication with one or more fourth electronic devices. For example, the first electronic device may transmit a position of the first electronic device to one or more fourth electronic devices, make a video emergency call with the one or more fourth electronic devices, and transmit information related to the streaming service established by the first electronic device to the one or more fourth electronic devices.

In operation 707, the first electronic device may identify that one or more fifth electronic devices which deal with the accident are added as counterparts of the first electronic device in the video emergency call. For example, the first electronic device may identify that police officers, firefighters, and emergency relief agents are added as the counterparts of the first electronic device in the video emergency call and the video emergency call switches to a video emergency conference call.

Figure 8:
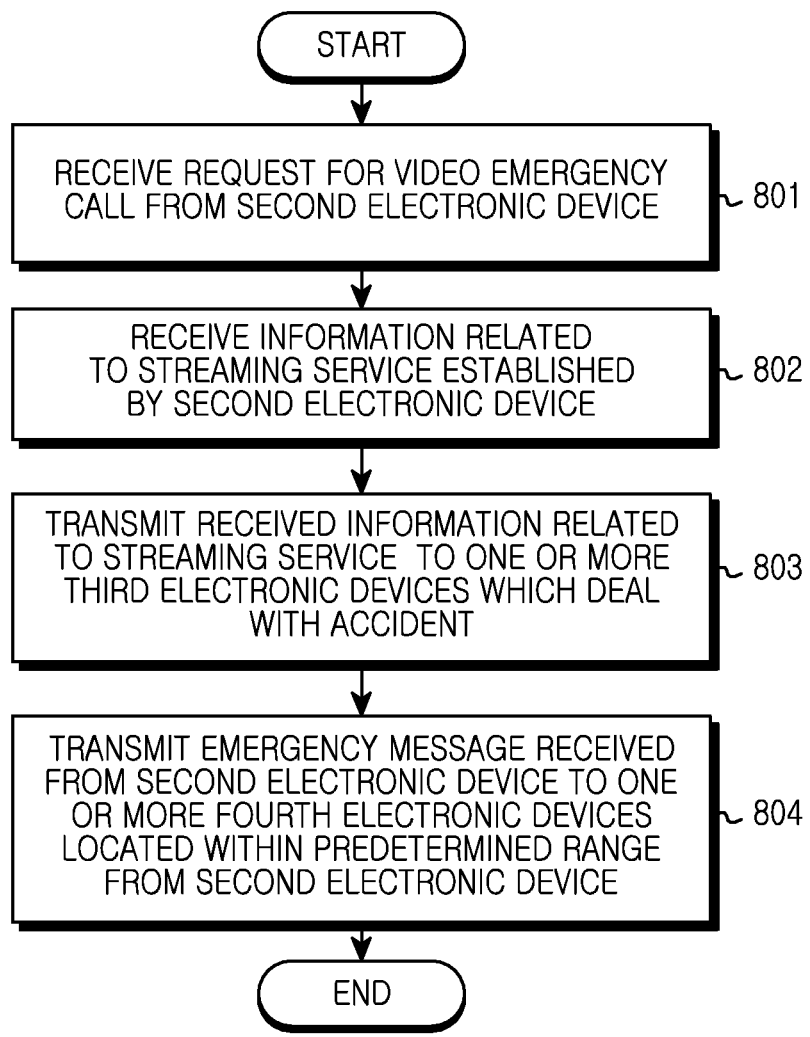
FIG. 8 is a flowchart illustrating an example process performed by a first electronic device having received a request for a video emergency call from a second electronic device of a user in an emergency situation according to various embodiments of the present disclosure.

FIG. 8 is a flowchart illustrating an example process performed by the first electronic device having received a request for a video emergency call from the second electronic device of the user in an emergency situation according to various embodiments of the present disclosure. In the following description, the second electronic device will be defined as an electronic device of the user in the emergency situation, a third electronic device will be defined as an electronic device of a user who is in charge of dealing with accidents, and a fourth electronic device will be defined as an electronic device located within a predetermined range from the second electronic device.

In step 801, the first electronic device may receive a request for a video emergency call from the second electronic device.

In operation 802, the first electronic device may receive information related to a streaming service established by the second electronic device. For example, the first electronic device may receive URL information of an established Internet broadcasting channel such as WWW.A.COM from the second electronic device. Address information of the Internet broadcasting channel received from the second electronic device may be used when the first electronic device automatically accesses the corresponding channel.

In operation 803, the first electronic device may transmit the received information related to the streaming service to one or more third electronic devices which deal with the accident. For example, the first electronic device may perform the video emergency call requested by the second electronic device, make a request for joining the video emergency call to the one or more third electronic devices which deal with the accident, and transmit the information related to the streaming service received from the second electronic device at the same time.

In operation 804, the first electronic device may transmit the emergency message received from the second electronic device to one or more fourth electronic devices located within a predetermined range from the second electronic device. For example, when the first electronic device receives a predetermined emergency message from the second electronic device, the first electronic device may transmit the received emergency message to one or more fourth electronic device located in the same cell as that including the first electronic device.

Figure 9:
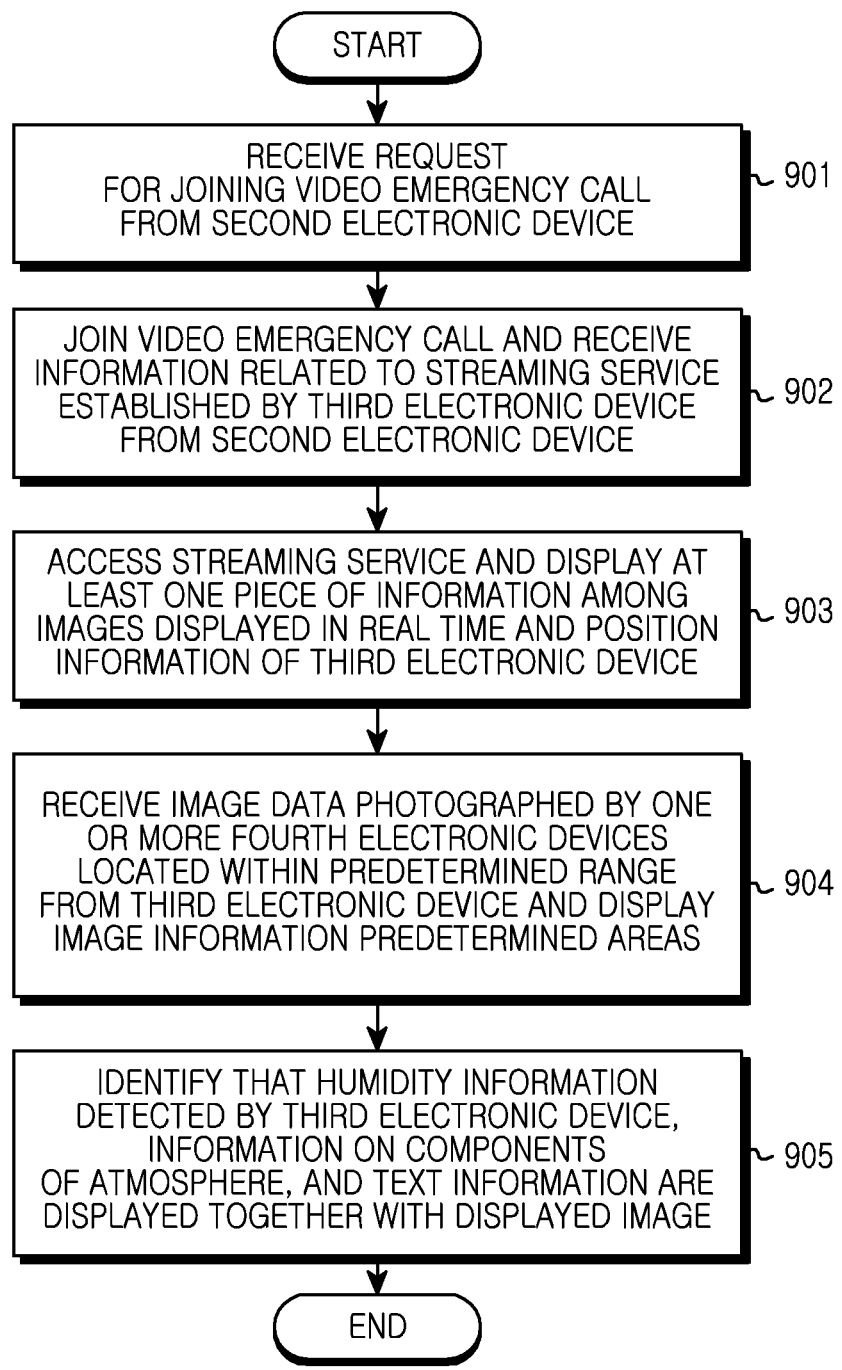
FIG. 9 is a flowchart illustrating an example process within first electronic device which performs accident processing according to various embodiments.

FIG. 9 is a flowchart illustrating an example process performed by a first electronic device which deals with accidents according to various embodiments of the present disclosure. In the following description, a second electronic device will be defined as an electronic device which receives a request for an initial video emergency call from a third electronic device, a third electronic device will be defined as an electronic device of a user in an emergency situation, and a fourth electronic device will be defined as an electronic device located within a predetermined range from the third electronic device.

In step 901, the first electronic device may receive a request for joining a video emergency call from the second electronic device. For example, the first electronic device may receive a request for joining a video emergency call from the second electronic device which is having the video emergency call with the third electronic device corresponding to the electronic device of the user in the emergency situation.

In operation 902, the first electronic device may join the video emergency call and receive information related to a streaming service established by the third electronic device from the second electronic device. For example, when the first electronic device joins the video emergency call in response to the request by the second electronic device, the first electronic device may receive URL information as the information related to the streaming service established by the third electronic device from the second electronic device.

In operation 903, the first electronic device may access the streaming service and display one or more pieces of information among images displayed in real time and position information of the third electronic device. For example, the first electronic device may receive image data associated with the site photographed at the position of the third electronic device and position information by using address information received from the second electronic device, and may display in real time the received image data and position information on the display of the first electronic device.

In operation 904, the first electronic device may receive image data photographed by each of one or more fourth electronic devices located within a predetermined range from the third electronic device and display the received image information in predetermined areas. For example, when one or more fourth electronic devices located in the same base station as that including the third electronic device exist, the first electronic device may receive image data associated with the accident scene photographed at positions of the one or more fourth electronic devices and display the image information in predetermined display areas.

In operation 905, the first electronic device may identify that humidity information detected by the third electronic device, information on components of atmosphere, and text information are displayed together with the displayed images. For example, the first electronic device may identify that humidity information detected by the third electronic device, information on components of atmosphere, and text information converted from a voice of the user of the third electronic device are displayed in a predetermined area of the display of the first electronic device.

Figure 10:
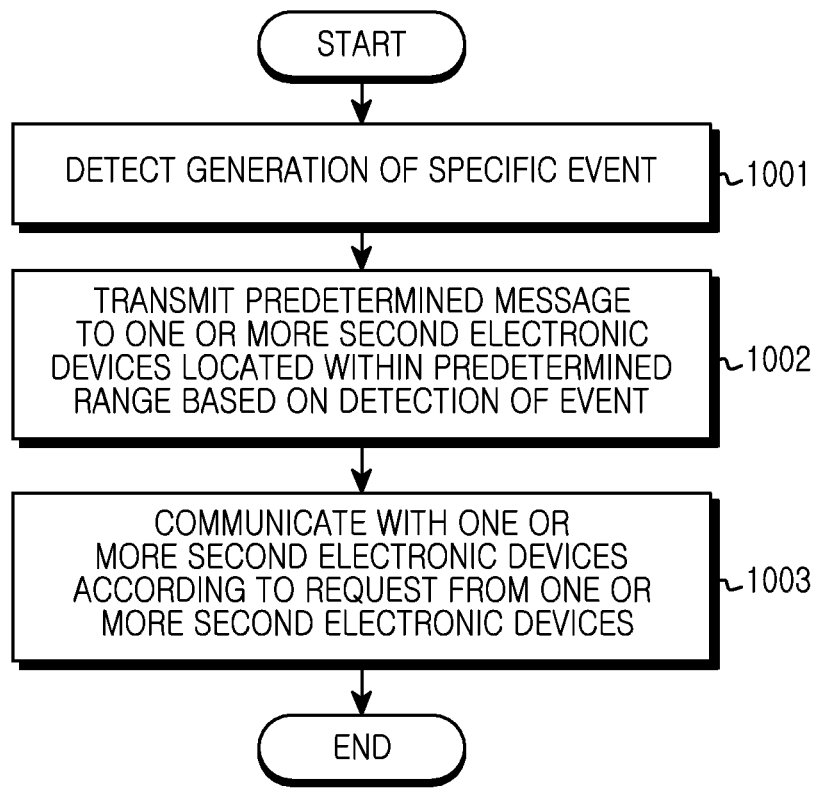
FIG. 10 is a flowchart illustrating an example method performed by a first electronic device according to various embodiments of the present disclosure of the present disclosure.

FIG. 10 is a flowchart illustrating an example method performed by a first electronic device according to various embodiments of the present disclosure. In operation 1001, the first electronic device may detect the generation of a specific event. According to various embodiments, the specific event may be an event for detecting the start of a streaming service, an event for detecting the transmission of an emergency call, an event for detecting that a user's heart rate received from another electronic device is larger than or equal to or equal to or smaller than a predetermined heart rate, or an event for detecting that an ambient temperature sensed using at least one sensor included in the first electronic device is higher than or equal to a predetermined temperature.

In operation 1002, when the first electronic device detects the generation of the specific event, the first electronic device may transmit a predetermined message to one or more second electronic devices located within a predetermined range. According to an embodiment, when the event for detecting the start of the streaming service occurs in the first electronic device, the first electronic device may transmit a predetermined emergency message to one or more second electronic devices located in the same base station as that including the first electronic device. According to an embodiment, after enabling a wireless communication module included in the first electronic device, the first electronic device may transmit a predetermined emergency message to one or more second electronic devices by using the enabled wireless communication module.

In operation 1003, the first electronic device may communicate with the one or more second electronic devices according to a request from the one or more second electronic devices. According to an embodiment, when the first electronic device receives a request for position identification information from one or more second electronic devices, the first electronic device may transmit current position information to the one or more second electronic devices. According to an embodiment, when the first electronic device receives a request for a video emergency call from one or more second electronic devices, the first electronic device may add the one or more second electronic devices as counterparts in the video emergency call. According to an embodiment, when the first electronic device receives a request for receiving images from one or more second electronic devices, the first electronic device may transmit image data photographed in real time to the one or more second electronic devices.

Figure 11:
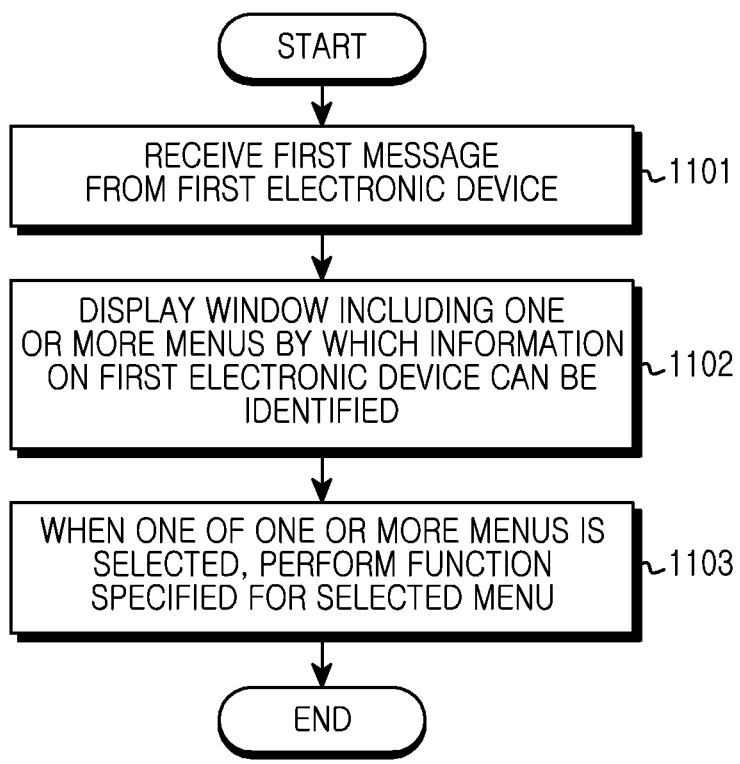
FIG. 11 is a flowchart illustrating an example method performed by a second electronic device according to various embodiments of the present disclosure.

FIG. 11 is a flowchart illustrating an example method performed by a second electronic device according to various embodiments of the present disclosure. In the following description, the second electronic device will be defined as an electronic device located within a predetermined range from the first electronic device.

In step 1101, the second electronic device may receive a first message from the first electronic device. For example, the second electronic device may receive an emergency message indicating that a user of the first electronic device is in an emergency situation from the first electronic device located in the same base station as that including the second electronic device.

According to various embodiments, the first message which the second electronic device receives from the first electronic device may be a trigger message for enabling a communication module of the second electronic device. According to an embodiment, when the second electronic device performs short-range communication with the first electronic device through Bluetooth, the message which the second electronic device receives from the first electronic device may include an ID of the first electronic device and a Bluetooth Media Access Control (MAC) address of the first electronic device. According to an embodiment, when the second electronic device performs short-range communication with the first electronic device through WiFi, the message which the second electronic device receives from the first electronic device may include an ID of the first electronic device and WiFi Service Set Identifier (SSID) information of the first electronic device. According to various embodiments, when the second electronic device receives a trigger message from the first electronic device, the second electronic device may enable a short-range communication module such as BT, BLE, or WiFi. According to an embodiment, the second electronic device may identify the ID of the first electronic device and information on the communication module to be used, included in the trigger message to search for the first electronic device. According to various embodiments, when the second electronic device discovers the first electronic device, the second electronic device may receive an emergency message from the first electronic device. According to an embodiment, the second electronic device may be connected to the first electronic device to receive the emergency message, or the emergency message may be included in a broadcast or beacon signal transmitted by the first electronic device before the second electronic device is connected to the first electronic device.

In operation 1102, the second electronic device may display a window including one or more menus by which information on the first electronic device can be identified. According to an embodiment, the windows displayed on the first electronic device may include menus such as a position identification menu, a video emergency call join menu, and an image reception menu.

In operation 1103, as the user selects one of the one or more menus in the first electronic device, the first electronic device may perform a function stored in the selected menu. According to an embodiment, when the user selects the "position identification menu" in the first electronic device, the first electronic device may display both current position information and an accident position corresponding to the position of the second electronic device on the display. According to an embodiment, when the user selects the "video emergency call" from the menus displayed on the first electronic device, the first electronic device may add the user as a counterpart in the video emergency call. According to an embodiment, when the user selects the "image reception menu" from the menus displayed on the first electronic device, the first electronic device may receive an image which is being photographed from the second electronic device and display the image in a predetermined area.

According to various embodiments of the present disclosure, a method of operating a first electronic device includes: detecting the generation of a specific event; detecting the event and transmitting a specific message to one or more second electronic devices located within a predetermined range; and performing communication with the one or more second electronic devices according to requests from the one or more second electronic devices.

The specific event may be an event for detecting a start of a streaming service.

The specific event may be an event for detecting transmission of an emergency call.

The specific event may be an event for detecting that a user's heart rate received from another electronic device linked with the first electronic device is larger than or equal to or equal to or smaller than a predetermined heart rate.

The specific event may be an event for detecting that an ambient temperature detected using at least one arranged sensor is higher than or equal to a predetermined temperature.

The transmitting of the specific message may include: enabling an arranged wireless communication module included in the first electronic device; and transmitting the specific message to the one or more second electronic devices by using the enabled wireless communication module.

The wireless communication module may include at least one of Bluetooth Low Energy (BLE), WiFi, or Bluetooth modules.

The method may further include enabling an arranged wireless communication module.

The message may include an ID of the first electronic device and a Bluetooth Media Access Control (MAC) address or WiFi Service Set IDentifier (SSID) information of the first electronic device.

The performing of the communication may include, when a request for position identification information is received from the one or more second electronic devices, transmitting current position information to the one or more second electronic devices.

The performing of the communication may include, when a request for a video emergency call is received from the one or more second electronic devices, adding the one or more second electronic devices as counterparts of the first electronic device in the video emergency call.

The method may further include identifying that the video emergency call switches to a video emergency conference call.

The performing of the communication may include, when a request for receiving images is received from the one or more second electronic devices, transmitting image data photographed in real time to the one or more second electronic device.

According to various embodiments of the present disclosure, a method of operating a second electronic device located within a predetermined range from a first electronic device includes: receiving a first message from the first electronic device; displaying a window including one or more menus by which information on the first electronic device can be identified; and when one of the one or more menus is selected, performing a function specified for the selected menu.

The method may further include: receiving an ID of the first electronic device and a Bluetooth Media Access Control (MAC) address or WiFi Service Set IDentifier (SSID) information of the first electronic device; receiving the information and enabling an arranged wireless communication module; and when the first electronic device is discovered, receiving a second message which is an emergency message.

The one or more menus include at least one of a position identification menu for identifying a position of the second electronic device, a video emergency call join menu for performing a video emergency call with the first electronic device, or an image reception menu for accessing an Internet broadcasting channel established by the first electronic device and displaying in real time an image photographed by the first electronic device.

The method may further include, when the video emergency call join menu for performing the video emergency call with the first electronic device is selected from the one or more menus, transmitting image data photographed using an arranged camera module to one or more third electronic devices which deal with accidents.

Figure 12:
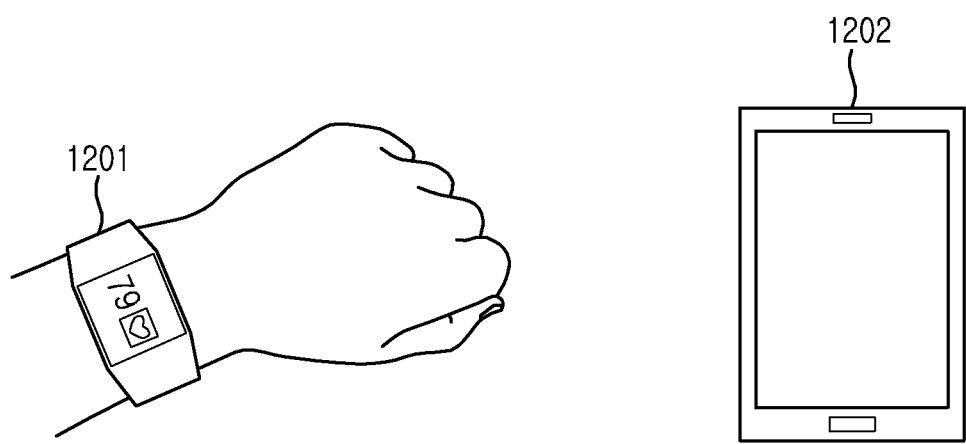
FIG. 12 is an example view describing a set event according to various embodiments of the present disclosure.

FIG. 12 is a view for describing a set event according to various embodiments of the present disclosure. According to various embodiments, when the first electronic device detects the generation of a specific event, the first electronic device may transmit a predetermined message to one or more second electronic devices located within a predetermined range from the first electronic device. According to an embodiment, the specific event detected by the first electronic device may be an event for detecting that a user's heart rate received from another electronic device linked with the first electronic device is larger than or equal to a predetermined heart rate, or smaller than or equal to a predetermined heart rate.

According to various embodiments, a first electronic device 1202 may receive information related to a user's heart rate received from an electronic device 1201 linked with the first electronic device 1202 worn on a user's wrist. According to an embodiment, the first electronic device 1202 may determine whether the user's heart rate is larger than or equal to or equal to or smaller than a predetermined heart rate by periodically identifying information on the user's heart rate received from the electronic device 1201 linked with the first electronic device 1202.

According to an embodiment, a case where the first electronic device 1202 periodically detects a user's heart rate and detects the generation of a specific event when the user's heart rate is larger than or equal to 150 or equal to or smaller than 80 will be described.

As illustrated in FIG. 12, when the user's heart rate is detected as 79 which is equal to or smaller than 80 based on a result of the periodical detection of the user's heart rate by the first electronic device 1202, the first electronic device 1202 may identify the generation of the specific event. According to various embodiments, the first electronic device 1202 may identify the generation of the specific event and transmit an emergency message to a second electronic device located within a predetermined range from the first electronic device 1202.

According to various embodiments, when the first electronic device 1202 measures a current altitude by using an altitude sensor included in the first electronic device 1202 and receives the user's heart rate from the electronic device 1201 linked with the first electronic device 1202, if the altitude is rapidly reduced and the user's heart rate is larger than or equal to or equal to or smaller than a predetermined heart rate, the first electronic device 1202 may determine that the user is falling and transmit an emergency message to the second electronic device.

According to various embodiments of the present disclosure, a method of operating an electronic device is disclosed, including: in response to detecting execution of an emergency call, establishing connections with at least a first external device and a second external device, executing the emergency call with the first external device, and transmitting media data (such as an image or a video) captured by the electronic device to the second external device for streaming.

According to various embodiments of the present disclosure, a method in an electronic device is disclosed, including: in response to receiving an emergency message from an external device, displaying selectable options for retrieving information related to the emergency message from the external device; and in response to detecting selection of one of the options, transmitting a corresponding request to the external device.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for". In addition, an artisan understands and appreciates that a "processor" or "microprocessor" may be hardware in the disclosure. Under the broadest reasonable interpretation, the appended claims are statutory subject matter in compliance with 35 U.S.C. § 101.

Meanwhile, the example embodiments disclosed in the specification and drawings are merely presented to easily describe the technical contents of the present disclosure and help the understanding of the present disclosure and are not intended to limit the scope of the present disclosure. Therefore, all changes or modifications derived from the technical idea of the present disclosure as well as the embodiments described herein should be interpreted to belong to the scope of the present disclosure.

What is claimed is:

1. A method of operating an electronic device, the method comprising:
    detecting that a heart rate of a user of the electronic device has exceeded at least one of a minimum or a maximum threshold;
    in response to detecting the heart rate of the user of the electronic device has exceeded at least one of a minimum or a maximum threshold:
    transmitting a message to initiate a phone call to a second electronic device, wherein the second electronic device displays a streaming video data using an associated Uniform Resource Locator (URL);

transmitting the streaming video data regarding the user generated by the electronic device to a device accessing the associated URL; and transmitting a predetermined textual message to at least one third electronic device located within a predetermined range of the electronic device; and providing the URL to one or more other electronic devices based on requests from the one or more other electronic devices.

2. The method of claim 1, wherein the transmitting of the message comprises:

enabling a wireless communication module included in the electronic device; and transmitting a specific message to the one or more other electronic device using the enabled wireless communication module.

3. The method of claim 2, wherein the wireless communication module includes at least one of Bluetooth Low Energy (BLE), WiFi, and Bluetooth modules.

4. The method of claim 1, wherein the message includes an ID of the electronic device and a Bluetooth Media Access Control (MAC) address or WiFi Service Set IDentifier (SSID) information of the electronic device.

5. The method of claim 1, further comprising transmitting position information to the one or more other electronic devices.

6. The method of claim 1, further comprising executing video emergency call with the one or more other electronic devices.

7. A method of operating an electronic device, the method comprising:

receiving a first message including a predetermined textual message from an external electronic device within a predetermined range of the electronic device;

displaying the received first message including a plurality of menus selectable to retrieve information related to the external electronic device, the plurality of menus including at least a video emergency call join option selectable to perform a video emergency call with the external electronic device, and an identify position option selectable to display a map indicating a position of the external electronic device relative to the electronic device; and in response to detecting selection of the video emergency call join option, joining a video call between the external electronic device and a third party electronic device.

8. The method of claim 7, further comprising:

receiving an identification of the external electronic device and a Bluetooth Media Access Control (MAC) address or WiFi Service Set IDentifier (SSID) information of the external electronic device;

enabling a wireless communication module; and when the external electronic device is discovered, receiving a second message which is an emergency message, wherein the plurality of menus of the received first message further includes a receive image option selectable to request a still image captured by the external electronic device and control the display to remove the plurality of menus and display the still image.

9. An electronic device, comprising:

a communication module; and a processor, configured to:

detect that a heart rate of a user of the electronic device has exceeded at least one of a minimum or a maximum threshold;

in response to detect the heart rate of the user of the electronic device has exceeded at least one of a minimum or a maximum threshold:

control the communication module to transmit a message to initiate a phone call to a second electronic device, wherein the second electronic device displays a streaming video data using the associated Uniform Resource Locator (URL);

control the communication module to transmit the streaming video data regarding the user generated by the electronic device to a device accessing the associated URL; and control the communication module to transmit a predetermined textual message to at least one third electronic device located within a predetermined range of the electronic device; and control the communication module to provide the URL to one or more other electronic devices based on a request from the one or more other electronic devices.

10. The electronic device of claim 9, wherein the communication module includes at least one of BLE, WiFi, and Bluetooth modules.

11. The electronic device of claim 9, wherein the message includes an ID of the electronic device and a Bluetooth Media Access Control (MAC) address or WiFi Service Set IDentifier (SSID) information of the electronic device.

12. The electronic device of claim 9, wherein the processor is configured to control the communication module to transmit position information to the one or more other electronic devices.

13. The electronic device of claim 9, wherein the processor is configured to control the communication module to execute video emergency call with the one or more other electronic devices.

14. An electronic device comprising:

a communication module;

a display; and at least one processor, configured to:

receive a first message including a predetermined textual message from an external electronic device within a predetermined range of the electronic device;

control the display to display the received first message including a plurality of menus selectable to retrieve information related to the external electronic device, wherein the plurality of menus comprise a video emergency call join option selectable to execute a video emergency call with the external electronic device and an identify position option selectable to display a map indicating a position of the external electronic device relative to the electronic device; and in response to detecting selection of the video emergency call join menu, control the communication module to join a video call including the external electronic device and a third party electronic device.

15. The electronic device of claim 14, wherein the communication module is configured to receive an identification of the external electronic device and a Bluetooth Media Access Control (MAC) address or WiFi Service Set IDentifier (SSID) information of the external electronic device, and receive a second message corresponding to an emergency message when the external electronic device is discovered, and wherein the plurality of menus of the received first message further includes a receive image option selectable to request a still image captured by the external electronic device and control the display to remove the plurality of menus and display the still image.

* * * * *